US009511016B2

(12) United States Patent
Oronsky et al.

(10) Patent No.: US 9,511,016 B2
(45) Date of Patent: Dec. 6, 2016

(54) TOPICAL COMPOSITION FOR TREATING PAIN

(75) Inventors: Bryan T. Oronsky, Los Altos Hills, CA (US); Neil C. Oronsky, Los Altos Hills, CA (US); Arnold L. Oronsky, Los Altos Hills, CA (US)

(73) Assignee: EpicentRx, Inc., Mountain View, CA (US)

( * ) Notice: Subject to any disclaimer, the term of this patent is extended or adjusted under 35 U.S.C. 154(b) by 1152 days.

(21) Appl. No.: 11/851,241

(22) Filed: Sep. 6, 2007

(65) Prior Publication Data
US 2008/0311167 A1 Dec. 18, 2008

Related U.S. Application Data

(60) Provisional application No. 60/943,552, filed on Jun. 12, 2007.

(51) Int. Cl.
*A61K 31/23* (2006.01)
*A61K 31/56* (2006.01)
*A61L 15/16* (2006.01)
*A61P 1/14* (2006.01)
*A61P 11/08* (2006.01)
*A61P 25/00* (2006.01)
*A61K 9/00* (2006.01)
*A61K 31/685* (2006.01)
*A61K 31/215* (2006.01)
*A61K 31/01* (2006.01)
*A61K 31/045* (2006.01)
*A61K 31/19* (2006.01)

(52) U.S. Cl.
CPC ........... *A61K 9/0014* (2013.01); *A61K 9/0009* (2013.01); *A61K 31/215* (2013.01); *A61K 31/685* (2013.01); *A61K 31/01* (2013.01); *A61K 31/045* (2013.01); *A61K 31/19* (2013.01); *A61K 31/23* (2013.01); *A61K 31/56* (2013.01)

(58) Field of Classification Search
None
See application file for complete search history.

(56) References Cited

U.S. PATENT DOCUMENTS

| 4,361,585 A | | 11/1982 | Edwards | |
|---|---|---|---|---|
| 4,405,616 A | * | 9/1983 | Rajadhyaksha | A61K 8/4906 514/212.03 |
| 5,260,313 A | * | 11/1993 | Frome | 514/552 |
| 5,538,740 A | * | 7/1996 | Abad | 424/547 |
| 5,885,597 A | | 3/1999 | Botknecht et al. | |
| 5,922,332 A | | 7/1999 | Fossel | |
| 6,132,762 A | | 10/2000 | Cristobal | |
| 6,528,076 B2 | * | 3/2003 | Small | 424/401 |
| 6,719,986 B1 | * | 4/2004 | Wohlrab | A61K 8/068 424/401 |
| 6,730,667 B2 | | 5/2004 | Deagle et al. | |
| 2002/0169195 A1 | * | 11/2002 | Kindness et al. | 514/406 |
| 2003/0082214 A1 | * | 5/2003 | Williams et al. | 424/400 |
| 2005/0077497 A1 | * | 4/2005 | Anderson | 252/299.1 |
| 2005/0123619 A1 | | 6/2005 | Farrell | |
| 2006/0280718 A1 | | 12/2006 | Roy et al. | |
| 2008/0102107 A1 | * | 5/2008 | Lewellyn et al. | 424/448 |

FOREIGN PATENT DOCUMENTS

| EP | 0325616 B1 * | 7/1994 | ........... A61K 9/0014 |
|---|---|---|---|
| WO | WO 89 11851 * | 12/1989 | |
| WO | WO-93/176945 A1 | 9/1993 | |
| WO | WO-95/15169 A1 | 6/1995 | |
| WO | WO 00 44367 * | 8/2000 | |
| WO | WO-01/87234 A2 | 11/2001 | |
| WO | WO-01/87234 A3 | 11/2001 | |
| WO | WO-2005/041988 A1 | 5/2005 | |

OTHER PUBLICATIONS

DiathermyWebsite.pdf (http://www.uihealthcare.com/topics/sportsmedicine/spor3327.html accessed Nov. 4, 2009).*
Dworkin, R. H. et al. (2007) Pain. 132; 237-251.*
Loeser, J. D. et al. (2008) Pain. 137; 473-477.*
Mayhew, M. S. (2008) J. Nurse Pract. 466-467.*
Goodman & Gilman's, 10th ed., p. 587, col. 1, lines 48-53.*
Napke, E., et al., Excipients and additives: hidden hazards in drug products and in product substitution, Can. Med. Assoc. J. (Dec. 15, 1984) pp. 1449-1452.*
Adams-Graves, P. et al. (1997). "RheothRx (Poloxamer 188) Injection for the Acute Painful Episode of Sickle Cell Disease: A Pilot Study," *Blood* 90(5):2041-2046.
International Search Report mailed on Apr. 9, 2009, for PCT Application No. PCT/US2008/084062, filed on Nov. 19, 2008, five pages.
Written Opinion of the International Searching Authority mailed on Apr. 9, 2009, for PCT Application No. PCT/US2008/084062, filed on Nov. 19, 2008, six pages.
Levy and Zochodne "Local Nitride Oxide Synthase Activity in a Model of Neuropathic Pain," *Eur. J. Neurosci.* 10(5):1846-(1998).
Walsh, "Safety and efficacy of topical nitroglycerin for treatment of vulvar pain in women with vulvodynia: a pilot study," http://www.ourgyn.com/content/index2.php?option=com_content&do_pdf=1&id=16, accessed Oct. 24, 2007.
Dodd, V. et al. (Jul. 2003). "Comparing the Use of Hydrogel Dressings to Lanolin Ointment With Lactating Mothers," *J. Obstet. Gynecol. Neonatal Nurs.* 32(4):486-494.
International Search Report mailed on Sep. 25, 2008, for PCT Application No. PCT/US2008/007354, filed on Jun. 11, 2008, three pages.

(Continued)

*Primary Examiner* — Bethany Barham
*Assistant Examiner* — Dominic Lazaro
(74) *Attorney, Agent, or Firm* — Goodwin Procter LLP

(57) ABSTRACT

Topical compositions having as the active ingredient a lipid, fatty acid ester, natural wax, sterol, or combinations thereof referred to herein as "lipophilic vehicle" or "LV" and methods of use, have been developed for the amelioration or prevention of pain or the sequelae of pain. The composition may be in the form of an ointment, cream, gel, lotion, spray, foam, paste, patch, suspension or dispersion. The composition is variably effective to treat visceral, somatic and neuropathic pain both acute and chronic as well as muscle pain and stiffness and joint pain and stiffness.

24 Claims, No Drawings

(56) References Cited

OTHER PUBLICATIONS

Murdan, S. (Jul.-Aug. 2005). "A Review of Pluronic Lecithin Organogel as a Topical and Transdermal Drug Delivery System," *Hospital Pharmacist* 12(7):267-270.
Rowley, T.J. et al. (Apr. 2005). "The Role of Adrenergic and Cholinergic Transmission in Volatile Anesthetic-Induced Pain Enhancement," *Anesth Analg.* 100(4):991-995.
Written Opinion mailed on Sep. 25, 2008, for PCT Application No. PCT/US2008/007354, filed on Jun. 11, 2008, six pages.
U.S. Appl. No. 12/138,300, filed Jun. 12, 2008, for Oronsky et al.
U.S. Appl. No. 12/138,304, filed Jun. 12, 2008, for Oronsky et al.
U.S. Appl. No. 12/140,080, filed Jun. 16, 2008, for Oronsky et al.
U.S. Appl. No. 11/942,409, filed Nov. 19, 2007, for Oronsky et al.
U.S. Appl. No. 12/139,223, filed Jun. 13, 2008, for Oronsky et al.
U.S. Appl. No. 12/140,086, filed Jun. 16, 2008, for Oronsky et al.

\* cited by examiner

TOPICAL COMPOSITION FOR TREATING PAIN

CROSS-REFERENCE TO RELATED APPLICATIONS

This application claims priority under 35 U.S.C. §119 to U.S. Ser. No. 60/943,552 filed Jun. 12, 2007.

FIELD OF THE INVENTION

The present invention relates to a topical treatment of acute and chronic pain, which is somatic, visceral, or neuropathic, as well as joint and muscle stiffness. This treatment also addresses to some degree the psychologic, vegetative and medication-induced sequelae of pain (usually chronic) which can include fatigue, decreased alertness, weight gain, decreased exercise tolerance, and dyspnea.

BACKGROUND OF THE INVENTION

Pain is a sensation and a perception that is comprised of a complex series of mechanisms. In its most simple construction, it is a signal from the firing of nociception, touch and pressure receptors in the periphery that is transmitted to the spinal cord and finally to lower and higher centers of the brain. However, this signal can be modified in a multitude of ways at each level of the pain pathway. See e.g. Millan, M. J. (1999) The Induction of Pain: An Integrative Review, Progress in Neurobiology, 57, 1-164 (Pergamon Press) for an in depth review.

There are primarily three types of pain, somatic, visceral and neuropathic which can be acute and chronic. Somatic pain is caused by the activation of pain receptors in either the cutaneous or musculoskeletal tissues. In contrast to surface somatic pain which is usually described as sharp and may have a burning or pricking quality, deep somatic pain is usually characterized as a dull, aching but localized sensation Somatic pain may include fractures in the vertebrae, joint pain (deep somatic pain) and postsurgical pain from a surgical incision (surface pain). Inflammatory pain shares elements in common with somatic, visceral and neuropathic pain since these conditions can induce inflammatory events. Inflammatory pain is related to tissue damage which can occur in the form of penetration wounds, burns, extreme cold, fractures, inflammatory arthropathies as seen in many autoimmune conditions, excessive stretching, infections, vasoconstriction and cancer.

Visceral pain is caused by activation of pain receptors in internal areas of the body that are enclosed within a cavity. An example of visceral pain, usually described as pressure-like, poorly localized and deep, is pancreatitis.

Neuropathic pain, caused by neural damage, is usually described as burning, tingling, shooting or stinging but can also manifest itself as sensory loss either as a result of compression, infiltration, chemical, metabolic damage or idiopathic. Examples of neuropathic pain are heterogenous and include medication-induced neuropathy and nerve compression syndromes such as carpal tunnel, radiculopathy due to vertebral disk herniation, post-amputation syndromes such as stump pain and phantom limb pain, metabolic disease such as diabetic neuropathy, neurotropic viral disease from herpes zoster and human immunodeficiency virus (HIV) disease, tumor infiltration leading to irritation or compression of nervous tissue, radiation neuritis, as after cancer radiotherapy, and autonomic dysfunction from complex regional pain syndrome (CRPS).

Acute pain, termed nociception, is the instantaneous onset of a painful sensation in response to a noxious stimulus. It is considered to be adaptive because it can prevent an organism from damaging itself. For example, removing a hand from a hot stove as soon as pain is felt can prevent serious burns. The second type of pain is persistent pain. Unlike acute pain, it usually has a delayed onset but can last for hours to days. It is predominately considered adaptive because the occurrence of persistent pain following injury can prevent further damage to the tissue. For example, the pain associated with a sprained ankle will prevent the patient from using the foot, thereby preventing further trauma and aiding healing. A third category of pain is chronic pain. It has a delayed onset and can last for months to years. In contrast to acute and persistent pain, chronic pain is considered maladaptive and is associated with conditions such as arthritis, nerve injury, AIDS and diabetes. Yet another type of pain can be termed breakthrough pain. This is a brief flare-up of severe pain lasting from minutes to hours that can occur in the presence or absence of a preceding or precipitating factor even while the patient is regularly taking pain medication. Many patients experience a number of episodes of breakthrough pain each day.

Many types of pain control are systemic in nature. These also have systemic side effects, such as stomach ulcers in the case of some of the non-steroidal anti-inflammatories ("NSAIDS"), hepatotoxicity from acetaminophen, constipation, CNS effects, respiratory depression, drug tolerance, dependence, and addiction from opioid narcotics and impotence and decreased libido from antidepressants. In the case of chronic pain, the side effects from these systemic medications sometimes can be controlled only with the addition more systemic medications which in turn have their own side effects such as the psychostimulant Ritalin to help counteract the symptoms of opioid-related drowsiness. In addition, the psychologic component of chronic pain can lead to fatigue, weight gain, increased appetite, decreased concentration and awareness, decreased energy, and psychomotor retardation which often require further adjunctive therapy such as antidepressants and stimulants. Associated comorbid conditions such as COPD, asthma, and hypertension can lead to dyspnea and decreased exercise tolerance, thereby exacerbating the downward spiral and depression which often characterizes chronic pain syndromes and necessitates further adjunctive treatment. Moreover, most topical treatments to control pain are of limited efficacy or last only for a few minutes, such as the lidocaine sprays and patches and benzocaine ointments.

Pain of all types can be debilitating both psychologically and physically and exacts an enormous toll in dollars, decreased productivity, and quality of life Therefore, formulations for prevention or alleviation of pain that are effective, safe, allow for increased levels of patient control, and in some measure affect the important psychologic, vegetative and medication-related sequelae of pain symptoms and treatment are needed in order to increase functionality and decrease the use of systemic medications with their attendant side effects.

It is therefore an object of the present invention to provide topical formulations providing pain relief for periods of varying durations lasting from minutes, to hours to days depending on the patient and the type of pain and painful lesion or syndrome.

SUMMARY OF THE INVENTION

Topical compositions having as the active ingredient one or more of a lipid, fatty acid ester, natural wax, sterol, or combinations thereof referred to herein as "lipophilic vehicle" or "LV" and methods of use, have been developed for the amelioration or prevention of pain or the sequelae of pain. The composition may be in the form of an ointment, cream, gel, lotion, spray, foam, paste, patch, suspension or dispersion. In the preferred embodiment, the formulation is a gel. The LV may contain a penetration enhancer, most preferably one with membrane disruptive properties.

The formulation may be applied to or impregnated into a gauze, wrap, bandage, cotton-tipped stick, adhesive bandage strip, or other support wrap or medical bandage or wound cover. For example, the compositions may be are incorporated onto or into disposables such as hemorrhoid wipes, sponge, mouth guards, dental trays; needles or catheters; adult diapers; gloves, socks or wrist bands, for ease of application.

The composition is applied topically to a site at or adjacent to a painful region. The composition is reapplied as necessary. Pain relief is typically obtained within minutes and lasts for periods of variable duration ranging from minutes to several hours and even, in some cases, days. The compounds are applied such that the dosage is sufficient to provide an effective dose in the painful area or immediately adjacent areas, to ameliorate or eliminate pain. The composition is variably effective to treat visceral, somatic, inflammatory and neuropathic pain both acute and chronic as well as muscle pain and stiffness and joint pain and stiffness. Examples demonstrate pain relief in human patients for a wide number of conditions, including joint, muscle and tendon pain, joint, muscle and tendon immobility, inflammatory pain, neuropathies, muscle spasms, osteoarthritis, breathing disorders such as wheezing, hunger pains, some types of headaches, dysphagia, fibromyalgia, autoimmune disorders, dysmennorhea, post-surgical pain, anal fissures and visceral pain resulting from chronic and pancreatitis.

DETAILED DESCRIPTION OF THE INVENTION

I. Definitions

"Water Soluble" as used herein refers to substances that have a solubility of greater than or equal to 5 g/100 ml water.

"Lipid Soluble" as used herein refers to substances that have a solubility of greater than or equal to 5 g/100 ml in a hydrophobic liquid such as castor oil.

"Hydrophilic" as used herein refers to substances that have strongly polar groups that readily interact with water.

"Lipophilic" refers to compounds having an affinity for lipids.

"Amphiphilic" refers to a molecule combining hydrophilic and lipophilic (hydrophobic) properties "Hydrophobic" as used herein refers to substances that lack an affinity for water; tending to repel and not absorb water as well as not dissolve in or mix with water.

An "oil" is a composition containing at least 95% wt of a lipophilic substance. Example lipophilic substances include but are not limited to naturally occurring and synthetic oils, fats, fatty acids, lecithins, triglycerides and combinations thereof.

An "emulsion" is a composition containing a mixture of non-miscible components homogenously blended together. In particular embodiments, the non-miscible components include a lipophilic component and an aqueous component. An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

"Emollients" are an externally applied agent that softens or soothes skin and are generally known in the art and listed in compendia, such as the "Handbook of Pharmaceutical Excipients", $4^{th}$ Ed., Pharmaceutical Press, 2003. These include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In one embodiment, the emollients are ethylhexylstearate and ethylhexyl palmitate.

"Surfactants" are surface-active agents that lower surface tension and thereby increase the emulsifying, foaming, dispersing, spreading and wetting properties of a product. Suitable non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In one embodiment, the non-ionic surfactant is stearyl alcohol.

"Emulsifiers" are surface active substances which promote the suspension of one liquid in another and promote the formation of a stable mixture, or emulsion, of oil and water. Common emulsifiers are: metallic soaps, certain animal and vegetable oils, and various polar compounds. Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxypropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

A "lotion" is an emulsion having a viscosity of between 100 and 1000 centistokes.

A "cream" is an emulsion having a viscosity of greater than 1000 centistokes, typically in the range of 20,000-50,000 centistokes.

A "paste" is a liquid or emulsion having solid material homogenously suspended therein, typically in a lotion cream or gel.

A "gel" is a composition containing a thickening agent or polymeric material dissolved or suspended in a liquid. The liquid may include a lipophilic component, an aqueous component or both. Some emulsions may be gels or otherwise include a gel component. Some gels, however, are not emulsions because some do not contain a homogenized blend of immiscible components.

"Penetration enhancers" are used to promote transdermal delivery of drugs across the skin, in particular across the stratum corneum. These can be chemical penetration enhancers or physical penetration enhancers, such as ultrasound.

Skin protectants can be included in compositions formulated for topical administration. Such agents not only soothe the site of infection but may also aide in maintaining the integrity of the skin to prevent additional damage. Suitable skin protectants include allantoin; cocoa butter; dimethicone; kaolin; shark liver oil; petrolatum; lanolin; vegetable oils; ethoxylated oils and lipids; polymers such as polyalkylene oxides, polyvinylpyrrolidone, polyvinyl alcohol, poly(meth)acrylates, ethylvinyl acetate, polyalkylene glycols; polysaccharides and modified polysaccharides such as hyaluronic acid, cellulose ethers, cellulose esters, hydroxypropyl methylcellulose, crosscarmelose, and starch; natural gums and resins which may be gelling or non-gelling such as alginates, carrageenans, agars, pectins, glucomannans (guar, locust bean, etc.), galactomannans (e.g. konjac), gum arabic, gum traganth, xanthan, schleroglucan and shellac; and colloidal insolubles such as zinc oxide and other insoluble zinc salts, talcum powder and other micronized natural minerals; and colloidal silicas, aluminas and other metal oxides.

Buffers are used to control pH of a composition. Preferably, the buffers buffer the composition from a pH of about 4 to a pH of about 7.5, more preferably from a pH of about 4 to a pH of about 7, and most preferably from a pH1 of about 5 to a pH of about 7. In a preferred embodiment, the buffer is triethanolamine.

Preservatives can be used to prevent the growth of fungi and microorganisms. Suitable antifungal and antimicrobial agents include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

II. Compositions

As demonstrated by the examples, it has been discovered that certain lipophilic vehicles can alleviate or prevent pain from a variety of different sources, when applied topically. Although the vehicles can also be used for drug delivery, drug is not required for efficacy.

A. Lipophilic Vehicles

Topical compositions having as the active ingredient a lipid (e.g., glycolipids, phospholipids), fatty acid ester, natural wax, sterol, and combinations thereof referred to herein as a "lipophilic vehicle" ("LV") have been developed and tested for alleviation of a variety of different types of pain. The formulation typically includes excipients that are amphiphilic, hydrophobic, lipophilic and/or surface active. These are used to form an ointment, cream, gel, lotion, spray, foam, paste, patch, suspension or dispersion, for topical application to the skin or mucosal surface. In the preferred embodiment, the formulation is a gel. The gel is preferably an organo gel.

The active ingredient can be a hydrophilic polymer, such as, in combination with a lipid, fatty acid ester, or sterol, or combinations thereof (e.g., PLO) or mono or diesters of a hydrophilic polymer (e.g., polyoxyl 40 stearate). Suitable LVs include Pluronic® F-127 gel containing lecithin and isopropyl myristate; Van Pen®; PCCA cosmetic HRT cream; a 50:50 mixture of ACAT Berry Blend and Aquaphor; mixtures of polyethylene glycol ("PEG"), glycerin, and isopropyl myristate; mixtures of lecithin and isopropyl myristate; pluronic gel; sesame oil; cottonseed oil; ointment base containing beeswax and lanolin; and detergents, such as Dawn®. Pluronic® F-127 is a polaxamer surfactant which is an ABA-type block copolymer containing 70% polyethylene oxide (PEO). The molecular weight is 12,500 Daltons. Upon cooling, Pluronic® F-127 becomes a liquid, while at higher temperatures, the material is a solid or semi-solid. DMSO and lecithin/isopropyl palmitate can be added to Pluronic® F-127 to increase absorption through the skin.

Additional LVs that provided pain relief include 20% pluronic gel+lecithin/isopropyl myristate+PEG+glycerin+pharmaceutical grade sesame oil; Oleic acid+AQUAPHOR™, VersaBase cream PCCA ("Professional Compounding Centers of America"), and PCCA Emollient Cream.

Lecithin

Lecithin is a mixture of glycolipids, triglycerides, and phospholipids (e.g. phosphatidylcholine, phosphatidylethanolamine, and phosphatidylinositol). Lecithin is also used as a synonym for pure phosphatidylcholine, a phospholipid which is the major component of a phosphatide fraction which may be isolated from either egg yolk or soy beans from which it is mechanically or chemically extracted using hexane.

Lecithin is regarded as a well-tolerated and non-toxic surfactant. It is approved by the United States Food and Drug Administration for human consumption with the status "Generally Recognized As Safe" (GRAS). Lecithin is an integral part of cell membranes, and can be completely metabolized by the body. Lecithin is used commercially in substances requiring a natural emulsifier and/or lubricant, from pharmaceuticals to protective coverings.

Isopropyl Myristate

Isopropyl myristate is the ester of isopropanol and myristic acid. It is a simple 12 carbon fatty acid ester. Isopropyl myristate is used in cosmetic and topical medicinal preparations where good absorption through the skin is desired.

Van Pen®

Van Pen® is a commercially available pharmaceutical base which contains soya lecithin, isopropyl palmitate, stearic acid, glycerol monostearate, isopropyl myristate, and polyoxyl 40 stearate. Soya lecithin and isopropyl myristate are described above.

Isopropyl palmitate is the ester of isopropanol and palmitic acid. Palmitic acid, is one of the most common saturated fatty acids found in animals and plants. As its name indicates, it is a major component of the oil from palm trees (palm oil and palm kernel oil). Palmitic acid is the first fatty acid produced during lipogenesis (fatty acid synthesis) and from which longer fatty acids can be produced. Palmitate negatively feeds back on acetyl-CoA carboxylase (ACC) which is responsible for converting acetyl-ACP to malonyl-ACP on the growing acyl chain, thus preventing further palmitate generation.

Glycerol fatty acid esters are used as emulsifiers or oiling agents for foods, spin finishes and textiles; antifoaming and antistatic agents for plastics; and lubricants, water treatment, metal working fluids, and dispersing agents. End applications include cosmetics, foods, personal care products, medicine, pesticides, paper making, plastics and paints.

Polyoxyl 40 Stearate is a mixture of the monostearate and distearate esters of a condensation polymer, $H(OCH2CH2)n-OCOC_{16}H_{32}CH_3$ (n is approximately 40). It is a nonionic surface-active agent used as an emulsifying agent in hydrophilic ointments and other emulsions.

PCCA Cosmetic HRT Cream

HRT cream is a base used for the formulation of cosmetics. HRT cream contains caprylic triglycerides; *macadamia* oil; grapeseed oil; and vitamin A palmitate.

Caprylic/capric triglyceride (CCT) is a mixture of triesters of caprylic and capric acids, is a highly refined medium chain triglyceride (MCT) oil possessing excellent oxidation stability with an almost indefinite shelf life. CCT is a desirable emollient with quick skin penetration. CCT is colorless, odorless, and tasteless.

*Macadamia* oil (or *Macadamia* nut oil) is a non-volatile oil expressed from the nut meat of the *macadamia* (*Macadamia integrifolia*) tree. *Macadamia* oil is sometimes used in food as a frying or salad oil, and in cosmetic formulations as an emollient or fragrance fixative. *Macadamia* oil contains approximately 60% oleic acid, 19% palmitoleic acid, 2.8% Linoleic acid and 1% Linolenic acid. It also contains 3% omega-6 and 3% omega-3. Although *macadamia* is cultivated in many different parts of the world, the oil's fatty acid profile is not greatly influenced by environmental factors. The oil displays chemical properties typical of a vegetable triglyceride oil.

Grape seed oil (also called grapeseed oil or grape oil) is a vegetable oil pressed from the seeds of various varieties of *Vitis vinifera* grapes, an abundant by-product of winemaking. Grape seed oil is used for in salad dressings, marinades, deep frying, flavored oils, baking, massage oil, sunburn repair lotion, hair products, body hygiene creams, lip balm and hand creams.

Grape seed oil is a preferred cosmetic ingredient for damaged and stressed tissues, possessing regenerative and restructuring qualities which allow for better control of skin moisturization. Grape seed oil can help skin retain the normal structure of epithelium cells and nerve cells via supporting the cell membranes. It is noted to be especially effective for repair of the skin around the eyes. Used as an all-over skin moisturizer, grape seed oil is known to reduce the look of stretch marks. A light, thin oil, grape seed oil leaves a glossy film over the skin when used as a carrier oil for essential oils in aromatherapy.

Grape seed oil contains 69-78% omega-6 (linoleic acid); 15-20% omega-9 (oleic acid); 5-11% palmitic acid; 3-6% stearic acid; 0.1-3% omega-3 (linolenic acid); and 0.5-0.7% palmitoleic acid. Grape seed oil contains more linoleic acid than many other carrier oils.

Retinyl palmitate, or vitamin A palmitate, is a common vitamin supplement, having the formula $C_{36}H_{60}O_2$. It is available in both oral and injectable forms for treatment of vitamin A deficiency, under the brand names Aquasol A® and Palmitate A®.

50:50 Acai Berry Blend+Aquaphor

This blend contains omega-6 and omega-9, which are discussed above. The blend also contains phytonutrients, phytosterols, polyphenolics and anthocyanins, vitamins, minerals, amino acids, antioxidants, anti-inflammatories, anti-mutagenics and anti-bacterials derived from the berry extracts. Aquaphor is a formulation containing 95% petrolatum.

Sesame Oil

Sesame Oil. (also known as gingelly oil and til oil) is an organic oil derived from sesame. Sesame oil is composed of the following fatty acids:

| Fatty acid | Nomenclature | Minimum | Maximum |
|---|---|---|---|
| Palmitic | C16:0 | 7.0% | 12.0% |
| Palmitoleic | C16:1 | trace | 0.5% |
| Stearic | C18:0 | 3.5% | 6.0% |
| Oleic | C18:1 | 35.0% | 50.0% |
| Linoleic | C18:2 | 35.0% | 50.0% |
| Linolenic | C18:3 | trace | 1.0% |
| Eicosenoic | C20:1 | trace | 1.0% |

Sesame oil is known for its ability to penetrate the skin easily, nourishing and detoxifying even the deepest tissue layers. Sesame oil is unique in that, it has the highest concentration of omega-6 fatty acids. The most common omega-6 fatty acids are linoleic, gamma-linolenic acid, eicosadienoic, dihomo-gamma-linoenic acid, arachidonic acid, docosadieoic acid, adrenic acid, and docosapentanoic acid. At the same time, the oil contains two natural-occurring preservatives, sesamol and sesamin. As a result, sesame oil is the only oil which has a high percentage of polyunsaturates that also keeps at room temperature.

Cottonseed Oil

Cottonseed oil is a vegetable oil extracted from the seeds of the cotton plant after the cotton lint has been removed. It must be refined to remove gossypol, a naturally occurring toxin that protects the cotton plant from insect damage. Therefore, unrefined cottonseed oil is sometimes used as a pesticide. In its natural unhydrogenated state, cottonseed oil, like all vegetable oils, has no cholesterol. It also contains no trans fatty acids. However, it does contain over 50% Omega-6 fatty acids and trace amounts of Omega-3 fatty acids. Cottonseed oil is rich in palmitic acid (22-26%), oleic acid (15-20%), linoleic acid (49-58%) and 10% mixture of arachidic acid, behenic acid and lignoceric acid.

Beeswax and Lanolin Ointment Base

Beeswax is obtains bee hives, specifically the hive of any species of honey bee (the genus *Apis*). The main components of beeswax are palmitate, palmitoleate, hydroxypalmitate and oleate esters of long-chain (30-32 carbons) aliphatic alcohols, with the ratio of triacontanylpalmitate $CH_3(CH_2)_{29}O—CO—(CH_2)_{14}CH_3$ to cerotic acid $CH_3(CH_2)_{24}COOH$, the two principal components, being 6:1.

Lanolin, also known as Adeps Lanae, wool wax, wool fat, or wool grease, is a greasy yellow substance obtained from wool-bearing animals. Lanolin is useful as a skin ointment, a water-proofing wax, and a raw material (such as in shoe polish).

Lanolin is chiefly a mixture of cholesterol and the esters of several fatty acids. Crude (non-medical) grades of lanolin also contain wool alcohols, which are an allergen for some people. Recent studies also indicate that antibiotics are present in the lanolin. The extract is insoluble in water, but forms an emulsion. At one point, the name Lanolin was trademarked as the generic term for a preparation of sheep fat and water.

Medical grade lanolin is used as a cream to soothe skin. It is pure, hypoallergenic, and bacteriostatic. This grade of lanolin can also be used to treat chapped lips, diaper rash, dry skin, itchy skin, rough feet, minor cuts, minor burns and skin abrasions. As an ointment base, it readily absorbs through skin, facilitating absorption of the medicinal chemicals it carries.

Lanolin is classified chemically as a wax, containing a complex mixture of naturally occurring esters and polyesters of 33 high molecular weight alcohols (principally sterols) and 36 fatty acids. It is 98% ester minimum, of which the fatty alcohols and fatty acids comprise an approximately 50/50 ratio.

The typical composition of lanolin is shown below:
Esters of sterols and triterpene alcohols 35.4%
Esters of aliphatic alcohols 23.7%
Monohydroxyesters of sterols and of triterpene and aliphatic alcohols 20.0%
Di- and polyhydroxyesters and free diols 7.9%
Free aliphatic alcohols 5.6%
Free Sterols 4.1%
Free hydrocarbons 0.6%
Free fatty acids 0.5%
Unknowns 2.2%

In a preferred embodiment, the LV penetrates into the skin. The LV may contain a penetration enhancer, most preferably one with membrane disruptive properties. One long-standing approach for improving transdermal drug delivery uses penetration enhancers (also called sorption promoters or accelerants) which penetrate into skin to reversibly decrease the barrier resistance. Numerous compounds have been evaluated for penetration enhancing activity, including sulphoxides (e.g., dimethylsulfoxide ("DMSO") and decylmethylsulfoxide (C10MSO)), Azones (e.g. laurocapram), pyrrolidones (for example 2-pyrrolidone, 2P), alcohols and alkanols (ethanol, or decanol), glycols (for example propylene glycol, PG, a common excipient in topically applied dosage forms), surfactants (also common in dosage forms) and terpenes. Many potential sites and modes of action have been identified for skin penetration enhancers, such as the intercellular lipid matrix in which the accelerants may disrupt the packing motif, the intracellular keratin domains, or through increasing drug partitioning into the tissue by acting as a solvent for the permeant within the membrane. Further potential mechanisms of action, for example with the enhancers acting on desmosomal connections between corneocytes or altering metabolic activity within the skin, or exerting an influence on the thermodynamic activity/solubility of the drug in its vehicle are possible.

Preferred penetration enhancers include the sulfoxide decylmethylsulfoxide ($C_{10}MSO$); ethers such as diethylene glycol monoethyl ether, delkaoxyethylene-oleylether, and diethylene glycol monomethyl ethers; surfactants, fatty acids such as C8-C22 and other fatty acids, C8-C22 fatty alcohols, and polyols. Other suitable penetration enhancers include, but are not limited to, urea, (carbonyldiamide), imidurea, N,N-diethylformamide, N-methyl-2-pyrrolidine, 1-dodecal-azacycloheptane-2-one, calcium thioglycate, 2-pyrrolidine, N,N-diethyl-m-toluamide, oleic acid and its ester derivatives, such as methyl, ethyl, propyl, isopropyl, butyl, vinyl and glycerylmonooleate, sorbitan esters, such as sorbitan monolaurate and sorbitan monooleate, other fatty acid esters such as isopropyl laurate, isopropyl myristate, isopropyl palmitate, diisopropyl adipate, propylene glycol monolaurate, propylene glycol monooleates and non-ionic detergents such as Brij® 76 (stearyl poly(10 oxyethylene ether), Brij® 78 (stearyl poly(20)oxyethylene ether), Brij® 96 (oleyl poly(10)oxyethylene ether), and Brij® 721 (stearyl poly (21) oxyethylene ether) (ICI Americas Inc. Corp.). Fatty acids such as linoleic acid, capric acid, lauric acid, and neodecanoic acid, which can be in a solvent such as ethanol or propylene glycol, can be used as lipid bilayer disrupting agents. DMSO is not a particularly preferred penetration enhancer due to its strong odor and the fact that it is not approved for use in humans by the Food and Drug Administration.

Detergents such as Dawn® detergent contain sodium lauryl sulfate, sodium pareth-23. Sodium dodecyl sulfate (or sulphate) (SDS or NaDS) ($C_{12}H_{25}NaO_4S$), also known as sodium lauryl sulfate (SLS), is an ionic surfactant that is used in household products such as toothpastes, shampoos, shaving foams and bubble baths for its thickening effect and its ability to create a lather. The molecule has a tail of 12 carbon atoms, attached to a sulfate group, giving the molecule the amphiphilic properties required of a detergent.

C. Drugs

The LV containing the penetration enhancer can be administered alone or in combination with another penetration enhancer or with a pharmaceutical agent, for example, one or more of vasodilators and antihypertensives, anticonvulsant, membrane stabilizer, and/or psychoactive drugs (for example, anti-depressants). Other classes of bioactives include chemotherapeutic agents for treatment of cancer, The LVs can be used in combination with antibiotics in cutaneous application to enhance delivery of antibiotic to wounds and to simultaneously provide pain relief. The LVs can be used in combination with chemotherapeutic agents in cutaneous application to enhance delivery of chemotherapeutic agents and to provide pain relief. The LVs can be used in combination with minerals such as calcium and phosphorus in cutaneous application in the treatment of osteoporosis or bone fractures to provide enhanced diffusion and pain relief. The LVs can be used in combination with adrenaline or noradrenaline in a cutaneous application to reduce pain and to cause localized vasoconstriction in order to keep another drug or substance in a localized space. The LVs can be used in combination with other appetite-suppressants and obesity medications such as phenteramine to enhance appetite-suppressing effects of LVs. Alternatively, the LVs can be used in combination with other appetite-stimulating medications such as Megace, corticosteroids, and Marinol to counteract appetite-suppressing effects of LVs. The LVs can be used in combination with bronchodilators, mucolytics, expectorants to enhance bronchodilating effects of LVs. The LVs can be used in combination with other decongestants and antihistamines both nasal and systemic to enhance decongestant effects of LVs. LVs can also be used in combination with other stimulant medications such as Provigil®, caffeine and Ritalin®, Adderal® 1 and Concerta® in order to enhance wakefulness-promoting effects of LVs. LVs can also be used in combination with other hypnotic or sedating medications to counteract wakefulness-promoting effects of LVs. LVs can be used in combination with other medications that increase the tightness of bladder neck sphincter such as Detrol to enhance the anti-incontinence effects of LVs. Alternatively, the LVs can be used in combination with other medications such as alpha-2 blockers to counteract the urinary retention induced by LVs. LVs can be administered in combination with immunosuppressive agents in cutaneous application directly over joints in autoimmune diseases and inflammatory arthropathies to provide diffusion of these agents directly into the joint or joints and to provide pain relief. LVs can be administered in combination with vasodilators in cutaneous application for anginal pain both to provide enhanced diffusion of these agents and to provide enhanced pain relief. LVs can be administered in combination with BoTox and other therapeutic toxins and antitoxins to provide localized pain relief and enhanced penetration. Finally, LVs can be administered in combination with corticosteroids and antihistamines in cutaneous application over joints, nerves and skin lesions such as psoriasis, eczema, scleroderma, urticaria to provide enhanced penetration and pain relief. In one embodiment, the LVs are provided in combination with dyes and other markers to provide enhanced penetration of dyes and markers along with pain relief.

The LVs may be applied topically directly before, after or simultaneously with a beta-2 agonist like albuterol or an anticholinergic like ipratropium bromide to enhance the effects of the LV.

An effective amount is generally in the range of 10% by weight or less, more preferably 5% by weight or less, most preferably in the range equivalent to 2% by weight of a nitrate such as nitroglycerin.

D. Formulations

The LVs can be administered directly or used in combination with a composition, device or formulation. For example, the LV can be impregnated onto or into bandages or adhesive strips such as Band-Aids®. These will then alleviate pain, prevent sticking to the wound, and allow the absorbent material to absorb liquid and protect the injury.

The LVs can be administered as a gauze, sponge, cotton swab (one or two sided or ended), wrap, patch, dressing, medication pad, tissue, pain-relief gel pack, lip balm, poultice, plaster, or compress.

The LVS can be applied within, on or in devices such as gloves, socks, wrist bands. The LVs can be impregnated into a wipe for use in alleviating pain from hemorrhoids or anal fissures. The gloves, socks or wristbands may have the formulation applied to the inside as a coating, impregnated into the fibers, or provided as a separate applicator for administration at the time of application. They may be applied as built-in or attach-on disposable pads to mattresses and pillows such as cervical pillows. The LVs may be applied to cushioned insoles and corn and bunion pads to help alleviate pain in the feet. The LVs may be applied on, in or to compression stockings such as TED hose or Jobst stockings to alleviate the pain of varicose veins and superficial thrombophlebitis.

The LVs may be used in facial tissues to soothe or prevent the sore or chapped skin under or around the nose with allergies or upper respiratory infections.

They may be used to coat medical instruments to ease the pain of their insertion and simultaneously to provide lubrication such as with a catheter.

They may be used to coat metal-containing items such as jewelry, hooks, zippers, pens, snaps and tools for individuals who have metal allergies and in particular nickel sensitivity.

They may be applied to mechanical braces, sleeves, corsets and girdles, splints, casts, prostheses and the like to provide analgesia along with the functional and positional support provided by the orthoses.

They may be applied as built-in or attach-on disposable pads to superficial heating devices such as electric heating pads, rubber hot water bottles, warm fluid heat packs, chemical hot packs and therapeutic cold modalities such as ice packs or added to vapocoolant sprays. They may be used in concert with modalities of electrotherapy such as iontophoresis, TENS, muscle stimulation, and diathermy or applied to the electrodes of these devices. They may be used in concert with radiation therapy such as infrared, ultraviolet and cold laser.

Examples of disposables include patches, hemorrhoid wipes, medication pads, dressings, gauze, sponges, bandages, tissues, wraps, pain-relief gel packs and beds, swabsticks and Q-tips, poultices, plasters and compresses; devices and equipment for injury protection, increased mobility, functional and positional support and correction such as orthotics, braces, TED hose and other support stockings, crutches, casts, splints, prosthetics, girdles and corsets, hot water bottles, inserts, insoles and arch supports, pads (e.g. corn and bunion) exercise equipment, cooling or heating devices, mattresses, pillows, chucks and bed liners and mouth guards; medical, dental and surgical implants, equipment and supplies such as dental trays, dental bridges, dentures, crowns, floss, picks, needles, lancets, rods, stents, blades, probes, stylets, tubes, scissors, clamps, retractors, forceps, endoscopes, mammography compression plates, cannulas or catheters; articles of clothing and footwear including shoes, shoelaces, socks, gloves, caps, scarves, leotards, head bands, wrist bands, gloves and adult diapers, pads, guards and liners. Additional materials include patches, bandages or dressings for use around the neck to decrease obstructive sleep apnea.

The LVs may be applied as built-in or attach-on disposable pads to mattresses and pillows such as cervical pillow. The LVs may be applied to bed underpads and chucks to alleviate the pain of bed sores and to promote continence. The LVs may be applied to cushioned insoles and corn and bunion pads to help alleviate pain in the feet. The LV may be applied on, in or to compression stockings such as TED hose or Jobst stockings to alleviate the pain of varicose veins and superficial thrombophlebitis.

The LVs may be applied to one end of a two-sided swabstick. The other end of the swabstick could contain a disinfectant like alcohol or iodine or an antihistamine or anti-inflammatory as well as antibiotics, chemotherapeutic agents, minerals and vitamins, appetite-suppressants and obesity medications such as phenteramine or appetite-stimulating medications such as Megace, immunosuppresive agents, vasodilators like nitrates, BoTox and other therapeutic toxins and antitoxins, dyes and other markers. The LVs may be applied to one side of a two-sided patch. The other side can contain antibiotics, chemotherapeutic agents, minerals and vitamins, appetite-suppressants and obesity medications such as phenteramine or appetite-stimulating medications such as Megace, corticosteroids, immunosuppresive agents, vasodilators like nitrates, BoTox and other therapeutic toxins and antitoxins, corticosteroids, antihistamines, dyes and other markers.

The may be used to coat a device such as a mouth guard, tray for whitening teeth or taking teeth impressions. Typically these will be applied as a paste, gel or film to the device at the time of use.

The LVs can be incorporated into cosmetics or makeup, to reduce inflammation or alleviate pain at the same time as covering up the inflammation or painful site.

The LVs can be incorporated into or onto or in a kit with needles or catheters or ports. This may be particularly advantageous with tattoo needles or piercing jewelry. These may be in the form of wipes or sponges that are applied to the skin at the time of or immediately before application of the needle, or even added to the tattoo ink or applied as a coating to the needle.

II. Methods of Treatment or Prevention

A. Methods of Administration

The composition is applied topically to a site at or adjacent to a painful region for both localized and systemic effects. The composition is reapplied as necessary. Pain relief is typically obtained within minutes and lasts for variable periods depending on the patient and type of pain symptoms. The compounds are applied such that the dosage is sufficient to provide an effective dose in the painful area or immediately adjacent areas, to ameliorate or eliminate one or more symptoms causing pain, or pain. The LV is applied to the skin, which may be rubbed in using an applicator, to the site of pain, as needed. Ultrasound or heat may also be applied to increase transdermal penetration and to increase local vasodilation.

As used herein, topical includes injection or infusion at the site of administration, for example, subcutaneously, and can include administration to mucosal surfaces, as well as trans-rectal, intra-peritoneal, intra-uterine and intraarticular.

Coadministration with an inhaled sympathomimetic such as albuterol or an inhaled parasympathomimetic such as ipratropium bromide tends to enhance the effects of the topical application.

B. Therapeutic Indications

The composition is generally effective to treat visceral, somatic and neuropathic pain both acute and chronic as well as muscle pain and stiffness and joint pain and stiffness. Examples include joint, muscle and tendon pain, joint, muscle and tendon immobility, inflammatory pain, neuropathies, muscle spasms, osteoarthritis, breathing disorders such as wheezing, hunger pains, some types of headaches, dysphagia, fibromyalgia, autoimmune disorders, and pancreatitis.

The composition also has an effect on some of the psychological and vegetative symptoms of pain, especially chronic pain, since in several patients, the LV alone without any active ingredient, applied to different areas on the skin can produce beneficial systemic effects such as decreased appetite, a feeling of heightened alertness, decongestion, increased energy and decreased fatigue, bronchodilation, urinary retention, and a sensation of decreased work of breathing. The composition has been demonstrated to provide pain relief in human patients for a wide number of conditions Indications for which the present formulations can be used include, but are not limited to, inflammatory arthropathies including rheumatoid arthritis, lupus and Reiter's syndrome, neuropathies including those resulting from pressure, medication and diabetes, bursitis, tendinopathies, sprains and muscle strains, joint pains and arthralgias, muscle stiffness and overuse syndromes, pancreatitis, dyspnea, wheezing and chest tightness induced by asthmas, atelectasis, high blood pressure, obesity and chronic obstructive pulmonary disease (COPD), tension headaches, pain from anal fissures, hunger pain, fractures or compression of lumbar vertebrae, fibromyalgia, chronic coccygeal pain, reflex sympathetic dystrophy, polyneuropathy, TMJ dysfunction, and osteoarthritis/degenerative joint disease, spondylosis.

The present invention will be further understood by reference to the following non-limiting examples. In the examples cited there was most often a significant decrease in the reported neuropathic pain, joint pain and stiffness, muscle pain and stiffness leading to increased mobility and range of motion of subjects receiving treatment of topically applied compounds as compared to subjects receiving placebo therapy. Also in subjects receiving treatment of topically applied compounds as compared to subjects receiving placebo therapy, a rubifacient effect on the skin, ranging from mild to pronounced in some cases, was also often observed. The first set of examples refers to treatment of patients with an LV usually in combination with an active agent. The second set of examples refers to treatment of patients with an LV alone and with an emphasis on the systemic effects observed both after administration of the LV to the affected painful area and to different non-involved cutaneous areas.

Example 1

Administration of LV with/without an Active Agent to Normal Control Human Patient Methods and Materials
a) Pluronic 20% with 750 mg lactose (Weise compounding pharmacy)
b) Vanpen (Weise compounding company)
c) PLO gel (Weise compounding company)—combination of soy lecithin (PCCA) dissolved in 20% pluronic gel made from 405 powder in a ratio of 25% lecithin to 75% pluronic gel
d) Lecithin soya dissolved in isopropyl myristate (Weise compounding company)
e) PLO (Advanced Rx compounding pharmacy)-combination of lactose (750 mg) with propylene glycol to we, 9 mL soy lecithin isopropyl palmitate and 20% pluronic gel (30 mg)
Atenolol (Advanced Rx compounding pharmacy)
Clonidine (Advanced Rx compounding pharmacy)
Nitrobid
Surgilube (applied as control)
Formulations were applied to skin with a tongue depressor.
Treatment and Observation
Application of (a) on skin resulted in numbness similar to that produced by lidocaine.
Application of (b) on skin led to slight numbness.
Application of (c) on skin resulted in pronounced numbness similar to lidocaine.
Application of (d) on skin had no effect.
Application of (e) on skin had a strong numbing effect but only after several minutes.

Example 2

Administration of LV with/without an Active Agent to Human Patient with Neck Pain Materials and Methods
Formulations were as in Example 1.
Patient presented with stiff neck with an inability to rotate it past 70 degrees to the right and a rotator cuff tendinopathy. Pain Level—4/10. Stiffness with an inability to move her shoulder past 70 degrees.
Treatment and Observation
Adding (e) resulted in a very slight effect on the shoulder.
Adding (c) reduced the pain to 3/10 and made shoulder more mobile.
Adding (d) seemed to have no effect.
Adding (e) plus Atenolol 25 mg dissolved in lactose, propylene glycol, soy lecithin/isopropyl palmitate, 20% pluronic gel had a strong effect reducing pain to 0.5/10 and made her shoulder much more mobile.
Adding to (e) clonidine 0.8 mg dissolved in lactose, propylene glycol, soy lecithin/isopropyl palmitate, 20% pluronic gel mixed with 2% nitrobid made the pain disappear completely and restored full mobility. In addition, the skin on her shoulder was red and patient stated that her shoulder felt flushed, warm and "good." Her neck became more mobile when (e) was then applied to it and she was able to turn her neck to 85 degrees. Subsequently applying (c) had no additional effect on mobility although it made the skin feel "numby." Adding clonidine 0.6 mg+nitrobid restored full 90 degrees mobility. Her pain-free interval and increased mobility lasted 1.5 weeks Example 3

Administration of LV with/without an Active Agent to Human Patient with Shoulder and Neck Pain from Tendonopathy Materials and Methods Formulations were the same as in Example 1.

The patient presented with Pain level=9/10 on shoulder/neck pain from a rotator cuff tendonopathy and inability to move his shoulder past the horizontal. Pain Level=7/10 left knee pain due to patellofemoral syndrome; Pain level=9/10 from a left sacroiliac strain.

Treatments and Observation

Shoulder: Applying 25 mg Atenolol dissolved in (e) decreased pain to 5/10 and patient noted that his skin felt warm and mobility was improved.

The clonidine+nitrobid combination was added with no change.

Then VanPen gel was added and pain disappeared with full mobility remaining.

Knee: Adding (e) decreased pain to 2/10 with no change in mobility. Clonidine 0.6 mg+nitrobid (2% nitrate) were applied with no change in pain or mobility.

Back (sacroiliac strain): Applied (e) and pain decreased to 5/10. Added clonidine+nitrobid and pain decreased to 4/10. Added VanPen and pain decreased to 3/10.

Example 4

Administration of LV with an Active Agent to Human Patient with Pain from Hammer Toes and Halux Valgus and Rigiditus Materials and Methods The same formulations were used as in Example 1.

Patient presented with a pain level of 7/10 for hammer toes and halux valgus and rigiditus. Because of the hallux rigiditus (rigid big toe) patient displayed virtually no movement in big toe.

Treatment and Observation:

After administering compound (e) patients pain decreased to 5/10 and patient was able to move the big toe where she previously could not. After adding Atenolol patient reported no effect. VanPen was then added and pain decreased to 3/10. Then nitrobid and 0.6 mg Clonidine were added and pain disappeared. Patient noted that for the first time in years she was able to walk without her cane.

Example 5

Administration of LV with an Active Agent to Human Patient with Pain from Trochanteric Bursitis, Knee Osteoarthritis Materials and Methods The same formulations were used as in Example 1.

The patient presented with a pain Level of 8/10 from trochanteric bursitis, and a pain level of 8/10 from knee osteoarthritis.

Treatment and Observation

Atenolol to hip reduced the pain level to 6/10. After applying clonidine 0.8 mg+nitrobid patient noted no change in pain level but the patient felt that the hip was much "looser." Application of Atenolol to knee decreased the pain level to 5/10. Overlying skin was flushed and patient stated that overall she felt "wonderful" and "better" than she had "in years."

Example 6

Administration of LV without an Active Agent to Human Patient with Pain from Tarsal Tunnel Syndrome Materials and Methods The same formulations were used as in Example 1.

The 37 year old male patient presented with a pain Level of 5/10 from symptoms consistent with tarsal tunnel syndrome.

Treatment and Observation

Lecithin Soya dissolved in isopropyl palmitate was applied to the patient's foot and the patient reported that the foot went numb to the point where it felt like it might "fall off" and pain was reduced to 0/10. Patient called 3 hours later to say that it was still numb.

Example 7

Administration of LV with/without an Active Agent to Human Patient with Pain from Fibromyalgia Materials and Methods The same formulations were used as in Example 1.

The 45 year old female patient with severe melancholic depression presented with Pain level=7/10 fibromyalgia with multiple bilateral tender sore spots.

Treatment and Observation

Applied different combinations of creams to different spots and overall patient stated that her pain level decreased to 5.75/10. Each of the creams either alone or in combination seemed to have varying effects working in some areas but not in others.

Example 8

Administration of LV with an Active Agent to Human Patient with Pain from Trochanteric Bursitis Materials and Methods The same formulations were used as in Example 1.

The 71 year old female patient presented with Pain level 8/10 from trochanteric bursitis; Pain level 10/10 from meralgia parsthetica or lateral femoral cutaneous neuropathy; Pain level 10/10 from right sacroiliac strain; and Pain level=5/10 from left rotator cuff tendinitis with almost no mobility.

Treatment and Observation

To 1 (hip) added Atenolol with no change. Then added VanPen and pain disappeared after several minutes.

To 2 (lat cut fem neuropathy) added pluronic acid 50%. Initially no change. Added 0.6 mg Clonidine+nitrobid and pain decreased to 5110.

To 3 (back) added clonidine 0.6 mg and pain decreased to 5-6/10. Added VanPen and after several minutes pain disappeared.

To 4 (shoulder) added clonidine 0.6 mg+nitrobid and pain decreased to 4/10. Added VanPen and pain decreased to 3/10. Also patient was able to fully move shoulder where she could not before.

In all cases after application of compounds the overlying skin took on a flushed, mottled appearance

Example 9

Administration of LV with an Active Agent to Human Patient with Pain from Right Sacroiliac Strain Materials and Methods The same formulations were used as in Example 1.

The 30 year old female patient presented with Pain level=6/10 from right sacroiliac strain, with radiation into the gluteal area and down right leg to the calf.

Treatment and Observation

After adding Clonidine 0.6 mg+nitrobid pain decreased to 3/10 with no soreness down leg. Patient noted a "deep numbing penetration." After adding VanPen patient noted complete numbness with no pain. Stated she felt "like dancing."

Example 10

Administration of LV with an Active Agent to Human Patient with Pain from Thoracalgia Materials and Methods The same formulations were used as in Example 1.

The 45 year old female patient presented with a pain level of 5/10 on both sides from thoracalgia versus costochondritis and symmetrical sore spots across her flanks radiating backwards circumferentially.

Treatment and Observation

VanPen was administered to the left side initially. Patient stated pain decreased to 3/10. Atenolol was administered to the right side and pain decreased to 2/10. Atenolol was then administered to the left side and VanPen administered to the right side, and pain completely disappeared from both sides as well as radiation around to back.

Example 11

Administration of LV with/without an Active Agent to Human Patient with Pain from Right Sacroiliac Strain Materials and Methods The same formulations were used as in Example 1.

The 51 year old African-American female patient presented with amputated right arm and a right arm neuroma with phantom limb with a pain level of 4/10.

Treatment and Observation

After applying VanPen, patient noted numbness and "dulling" of the pain to 2/10. After adding Clonidine 0.8 mg pain completely disappeared.

Example 12

Administration of LV with an Active Agent to Human Patient with Pain from Osteoarthritis Materials and Methods Clonidine paste was applied at a dose of about 0.3 mg per site, Nitrobid paste was applied from around 0.5 inches to 1 inch per site, viscous lidocaine 2% and topical capsaicin (which did not have much of an effect except in a few patients) were applied without regard to amount.

Treatment and Observation

The 70 year old female presented with right knee osteoarthritis with a pain level of 10/10. Nitrobid paste was applied to the knee. The pain level decreased to 0 in about 5 minutes. Patient remained pain-free for about 1 week.

Example 13

Administration of LV with an Active Agent to Human Patient with Pain from Cervical Strain Materials and Methods The formulations were as described in Example 1.

The 47 year old female presented with cervical strain with a pain level of 9/10. Nitrobid paste was applied to the neck.

Treatment and Observation

Pain decreased to 0 within 10 minutes and had not yet returned in over a month

Example 14

Administration of LV with an Active Agent to Human Patient with Pain from Osteoarthritis Materials and Methods The formulations were as described in Example 1.

The 45 year old female presented with bilateral knee osteoarthritis with a pain level of 10/10. Nitrobid paste was applied to the knees Treatment and Observation The pain decreased to 0 within 10 minutes. Pain relief lasted for 12 hours.

Example 15

Administration of LV with an Active Agent to Human Patient with Pain from Trochanteric Bursitis Materials and Methods The formulations were as described in Example 1.

The 50 year old male patient presented with right trochanteric bursitis (hip) with a pain level of 7/10, and lateral epicondylitis (elbow) with a pain level of 8/10. Nitrobid paste was applied to lateral epicondyle and greater trochanter.

Treatment and Observation

The pain decreased to 0 in the hip and elbow within 10 minutes. Patient stated his hip felt so much better he wanted to "dance." Patient was pain-free for about 6 hours.

Example 16

Administration of LV with an Active Agent to Human Patient with Pain from Torticollis Materials and Methods The formulations were as described in Example 12.

The 42 year old male patient presented with torticollis. The pain level was 9/10 with extreme stiffness and inability to turn head more than 20 degrees to either side. Nitrobid cream was applied to neck.

Treatment and Observation

Pain decreased from 9/10 to 6/10. Patient's neck also became more supple and range of movement went from about 20 degrees turning to either side to over 70 degrees. No follow-up available as yet.

Example 17

Administration of LV with an Active Agent to Human Patient with Pain from Bursitis Materials and Methods The formulations were as described in Example 12.

A 36 year old male presented with a left rotator cuff impingement and bursitis with a pain level of 5110.

Treatment and Observation

Pain disappeared with 0.8 mg of clonidine.

Table 1 shows the application of nitrobid paste and clonidine paste in series.

TABLE 1

Administration of nitrobid and clonidine paste

I. Treatment with nitronid (NB) followed by clonidine paste (CD) 0.3 mg

| Patient | Patient Complain | Initial | NB | CD |
|---|---|---|---|---|
| 1 | Migraines and tension headaches | 6/10 | 5/10 | 0/10 |
| 2 | Sacroiliac strain | 810 | 7/10 | 3/10 |
| a3 | Neck Spondylosis | 5/10 | 3/10 | 0/10 |
| 4 | Sacroiliac strain | 9/10 | 6/10 | 5/10 |
| b5 | Sacroiliac strain | 6/10 | 5/10 | 4.75/10 |
| b6 | Torn rotator cuff | 6/10 | 3/10 | 0/10 |

II. Treatment with clonidine paste (CD) followed by nitrobid paste (NB)

| | | Initial | CD | NB |
|---|---|---|---|---|
| 1 | Neck spondylosis | 5/10 | 3/10 | 0/10 |
| 2 | Osteoarthritis | 10/10 | 7/10 | 3.5/10 |
| 3 | Osteonecrosis of hip | 9/10 | 6/10 | 3/10 | aPatient later developed a splitting headache as a side effect
bPatient also had increased flexibility; overlying skin became flushed Example 18

Administration of LV with an Active Agent to Human Patient with Pain from Torn ACL and Meniscus Materials and Methods The formulations were as described in Example 12.

A 45 year old female presented with torn right ACL and torn meniscus in right knee and anterior tarsal tunnel syndrome (a compressive neuropathy) in right ankle. Capsaicin and lidocaine were applied to knee and ankle.

Treatment and Observation

There was a decrease in pain from 8/10 to 7.5/10 in the knee and no change in pain level in the ankle. After nitrobid paste was added, pain decreased in the knee to 5/10, and pain and paresthesias disappeared in ankle to 0/10.

Example 19

Administration of LV with an Active Agent to Human Patient with Pain from Torn Rotator Cuff Materials and Methods The formulations were as described in Example 1.

The 51 year old male presented with osteoarthritis bilaterally of knees and a torn right rotator cuff and frozen shoulder. The pain level was 10/10 in left knee, 7/10 right knee and 5/10 in right shoulder. The right shoulder demonstrated decreased abduction of about 50 degrees and decreased external rotation of about 60 degrees.

Treatment and Observation

After addition of a mixture of topical capsaicin and 2% viscous lidocaine, patient's pain decreased to 7/10 in left knee, to 3/10 in right knee and 3/10 in right shoulder. With addition of nitrobid paste, pain further decreased to 5/10 in left knee, and to 0/10 in right knee and right shoulder. Furthermore, patient had increased mobility and range of movement of shoulder increased in abduction to about 70 degrees and increased external rotation to about 80 degrees.

Example 20

Administration of LV with an Active Agent to Human Patient with Pain from Joint Pain Materials and Methods The formulations were as described in Example 1.

A 55 year old female presented with a right knee replacement with patellofemoral syndrome and osteoarthritis, with a pan level of 8/110, patellofemoral syndrome and likely osteochondritis dessicans (loose body) in left knee with a pain level of 9/10, carpal tunnel syndrome of right wrist with complaints of pain and paresthesias in 1st two fingers of hand, with a pain level of 9/10, ischial gluteal bursitis with a pain level of 9/10 and trochanteric bursitis with a pain level of 9/10. Nitropaste was added to left knee and right wrist.

Treatment and Observation

Pain in the left knee went from a 9/10 to a 4/10 after about 10 minutes. Pain in the right wrist (carpal tunnel) went to 4/10 after about 20 minutes. At about 30 minutes, clonidine paste was added to right wrist and left knee, and pain decreased to 3/10 in the wrist and O/10 in left knee. For right knee osteoarthritis, left trochanteric bursitis and ischial gluteal bursitis, clonidine was first added to right knee, left greater trochanter and ischial tuberosity and pain decreased in right knee from 9/10 to 8/10, in ischial tuberosity from 9/10 to 5/10, and greater trochanter from 9/10 to 5/10 all within 10 minutes. Then nitropaste was applied and pain from ischial gluteal bursitis decreased 1/10, pain from trochanteric bursitis decreased to 1/10 and pain from right knee osteoarthritis decreased to 6/10. The overlying skin where compounds were applied became red and mottled.

Example 21

Administration of LV with an Active Agent to Human Patient with Pain from Bilateral Sacroiliac Strain Materials and Methods The formulations were as described in Example 12.

The 70 year old female presented with bilateral sacroiliac strain. Pain level was 9/10 and patient had abnormal Scober test with stiffness to lumbosacral region.

Treatment and Observation

Nitrobid paste was applied to sacroiliac joints bilaterally and pain level decreased to 6/10 within 10 minutes. Then Clonidine paste was applied and pain level decreased to 5/10. Patient also had improved mobility and range of motion and was able to bend forward almost touching her toes

Example 22

Administration of LV with an Active Agent to Human Patient with Pain from Bilateral Rotator Cuff Tear

Materials and Methods
The formulations were as described in Example 12.
A 65 year old male presented with a bilateral rotator cuff tear with a pain level of 8.5410.
Treatment and Observation
Clonidine alone applied on right shoulder and nitrobid on left shoulder separately had no effect. When clonidine and nitrobid were combined in a single formulation and applied on both shoulders, the patient reported a decrease in pain level to 7/10 in both shoulders.

Example 23

Administration of LV with an Active Agent to Human Patient with Pain from Thoracalgia with No Efficacy

Materials and Methods
The formulations were as described in Example 12.
A 51 year old patient presented with thoracalgia with a pain level of 8/10.
Treatment and Observation
He reported no effect with application of either the clonidine or nitrobid or capsaicin and lidocaine or a combination of all three.

Example 24

Administration of LV with an Active Agent to Human Patient with Pain from Patellofemoral Syndrome

Materials and Methods
The formulations were as described in Example 12.
A 46 year old male with left patellofeemoral syndrome presented with a pain level of 7/10.
Treatment and Observation
Application of Nitrobid reduced pain to 5/10 and then application of clonidine 0.8 mg reduced further reduced the pain to 3/10. A day later patient reported that his knee pain was still reduced

Example 25

Administration of LV with an Active Agent to Human Patient with Pain from Trochanteric Bursitis

Materials and Methods
The formulations were as described in Example 12.
A 64 year old man presented with left trochanteric bursitis with a pain level of 7/10, low back pain secondary to a lumbar compression fracture with a pain level of 7/10 and right thumb osteoarthritis with a pain level 2/10.
Treatment and Observation
With application of clonidine 0.8 mg, thumb pain stayed the same after 5 minutes but with application of nitrobid 2% it disappeared. With a combination of nitrobid and clonidine back pain also disappeared. Trochanteric bursitis disappeared with just application of clonidine.

Example 26

Administration of LV with an Active Agent to Human Patient with Pain from Compression Fracture of Vertebra

Materials and Methods
The formulations were as described in Example 12.
A 49 year old female presented with a vertebral compression fracture of L3 with a pain level of 6/10.
Treatment and Observation
1.6 mg of clonidine was applied to lower back and pain level decreased to a 4/10. No change was observed with application of nitropaste. The improvement lasted 6 hours and the patient reported that she was able to sit for a prolonged period for the first time in several months.

Example 27

Administration of LV with an Active Agent to Human Patient with Pain from Neck Stiffness

Materials and Methods
The formulations were as described in Example 12.
A 41 year old male presented with neck stiffness and pain secondary to radiculopathy. Pain level was about 6/10.
Treatment and Observation
After application of clonidine 0.8 mg pain disappeared but patient was only able to rotate head 70 to left and 75 degrees to right. After application of nitropaste patient was able to rotate head 85 degrees to the right and 80 degrees to left

Example 28

Administration of LV with an Active Agent to Human Patient with Pain from Osteoarthritis

Materials and Methods
The formulations were as described in Example 12.
A 50 year old female presented with bilateral osteoarthritis and patellofemoral syndrome of knees with a pain level of 6/10 in both knees and inability to flex the knees because of pain.
Treatment and Observation
Clonidine was applied to the right knee and pain decreased to 3/10. To left knee nitrobid was added and pain level stayed roughly the same. After addition of nitrobid to right knee pain disappeared and ability to flex knee became much improved. After addition of clonidine to left knee pain also disappeared and patient demonstrated improved flexibility. 2 days later the patient was still pain-free.

Example 29

Administration of LV with an Active Agent to Human Patient with Pain from Lupus and Disc Bulges

Materials and Methods
The formulations were as described in Example 12.
A 40 year old woman presented with systemic lupus and multilevel disc bulges with a pain level of 6/10 on presentation.

Treatment and Observation

With application of 0.8 mg clonidine and 2% nitrobid paste to back, pain diminished to 5/10 and patient reported slightly improved flexibility.

Example 30

Administration of LV with an Active Agent to Human Patient with Pain from Neuropathy Materials and Methods The formulations were as described in Example 12.

A 51 year old diabetic with lower extremity neuropathy and severe vascular stenosis presented with a pain level of 7/10.

Treatment and Observation

Clonidine 0.8 mg was applied to legs and pain level decreased to 5/10 in 5 minutes. Then, nitrates were added and pain disappeared.

Example 31

Administration of LV Combined with an Active Agent to Human Patient with Pain from Cluster Headache Materials and Methods The formulations were as described in Example 12.

A 50 year old man presented with cluster headaches with an intractable headache and wearing dark sunglasses with a pain level of 10/10.

Treatment and Observation

Application of Clonidine 1.6 mg combined with 2 inches of 2% nitroglycerin lead to complete disappearance of headache Example 32

Administration of LV with an Active Agent to Human Patient with Pain from Headache Materials and Methods The formulations were as described in Example 12.

A 94 year old female presented with a unilateral migraine characterized by photophobia, phonophobia, nausea, vomiting and with a pain level of 10/10. She stated that the headache originated from her neck.

Treatment and Observation

Clonidine 0.1 mg combined with 0.5 inches of 2% Nitrobid applied to back of neck resulted in diminishment of pain from headache to 3/10

Example 33

Administration of LV with an Active Agent to Human Patient with Pain from TMJ

Materials and Methods

The formulations were as described in Example 12.

A 41 year old male presented with trigeminal neuralgia, temporal mandibular joint dysfunction and hemicrania continua. The pain level was 8/10.

Treatment and Observation

Premixed cream was applied and within 10 minutes patients pain level decreased to 2/10.

Example 34

Administration of LV with an Active Agent to Human Patients

I. Administration of Atenolol in PLO (a) Administration to a Patient with Pain from Rotator Cuff Tendinopathy Male patient presented with rotator cuff tendinopathy and shortness of breath. The pain level was 8/10.

Atenolol in PLO was applied to shoulder, and back and pain level decreased to 0/10. Patient also noted that breathing improved.

(b) Administration to a Patient with Wheezing

Female African-american patient presented in visible respiratory distress, audibly wheezing and using an albuterol inhaler every few minutes.

Atenolol in PLO gel was applied to back and chest. Within a few minutes the wheezing abated and patient no longer needed to use the inhaler for at least 20 minutes while the patient was in the office II. Administration of 0.6 mg Clonidin+Nitrobid (a) Administration to a Patient with Pain from Biceps Insertionitis African-american male patient presented with biceps insertionitis. The pain level was 6/10.

Clonidine 0.6 mg+nitrobid were premixed and applied to the biceps tendon. Pain level decreased to 1/10 and patient noted that his arm felt much more mobile.

(b) Administration to a Patient with Bilateral Sacroiliac Strain

Male patient presented with low back pain, with a pain level of 6/10.

Clonidine 0.6 mg premixed with nitrobid was applied to sacroiliac joints. Patient's pain diminished from 6/10 to 2/10 only 2-3 hours later but the interval with diminished pain lasted 24 hours.

(c) Administration to a Patient with Patient with a Left Rotator Cuff Tendinopathy Male patient presented shoulder pain, with a pain level of 6/10.

Application of Clonidine 0.6 mg premixed with nitrobid followed by VanPen cream and further followed by Pluronic gel 20% with lecithin soya/isopropyl myristate had no effect on patient's pain.

III. Administration Pluronic Gel+Nitrobid (a) Administration to a Patient with Back and Leg Pain Male patient presented with severe pain in back and legs. The pain level was 10/10.

Pluronic gel 20% with lecithin soya and nitrobid were premixed and applied to both of the patients' legs. Patient stated that there was no change in pain level.

(b) Administration to Patients with Joint Pain

Female patient presented with malaise, weakness, myalgias, tendinopathies and extreme diffuse joint pain, with a pain level of 10/10.

Pluronic gel 20% with lecithin soya/isopropyl myristate premixed with nitrobid was applied to shoulders, neck, hips, wrists, hands, knees and ankles. Patient reported that her pain dissipated to 0/10 and lasted for 4 hours before returning. She also noted that during these 4 hours, she felt more alert and awake, breathed easier and was less hungry.

Male patient with severe rheumatoid arthritis presented with diffuse joint pain, with a pain level of 10/10.

Pluronic gel 20% with lecithin soya/isopropyl myristate premixed with nitrobid was applied to shoulders, hands, wrists, and elbows. Patient reported that his pain in these joints dissipated to 0/10 and lasted for about 7.5 hours before returning. He also noted that he felt more alert and awake.

(c) Administration to Patient with Thoracalgia

Male patient with pain in the chest. The pain level was 6/10.

Pluronic gel 20% with lecithin soya/isopropyl myristate premixed with nitrobid was applied to mid/upper back. Patient reported that his back pain disappeared.

IV. Administration of Orajel (a) Administration to a Patient a Teeth Pain and Diabetic Neuropathy Female patient presented with mouth pain with a pain level of 10/10 and painful diabetic neuropathy with a pain level of 7/10.

After administration of Orajel (PEG+benzocaine), patient noted not only decreased mouth pain but also markedly decreased pain in his lower extremities from 7/10 to 2/10. The relief in his lower extremities lasted about 30 minutes before returning.

(b) Administration to a Patient with Wrist and Neck Pain

Male patient presented with wrist pain with a pain level of 7/10 and neck pain with a pain level of 5/10.

Oragel applied to the gums decreased his neck pain from 2/10 (brought to these levels by administration of PEG) to 1/10.

V. Administration of PLO Gel Followed by Albuterol and/or Ipratropium Bromide (Atrovent)

(a) Administration to a Patient with Diabetic Nephropathy

Patient presented with diabetic nephropathy complained of stinging, shooting, lacinating pains in bilateral lower extremities worse over the heels in intensity. The pain level was 8/10.

PLO gel was applied to right heel and pain level dropped to 5/10, with no change in left heel. 5 minutes later patient was given albuterol inhaler, within 30 seconds pain in right heel dropped to 4/10 and pain in left heel dropped to 6/10. 5 minutes later he was given an Atrovent inhaler and within 30 seconds pain in right heel dropped to 3/10 and pain in left heel dropped to 5/10. He was given albuterol inhaler again and pain in right heel dropped to 2/10 and pain left heel dropped to 3/10. No further change occurred with inhalers but patient noted that, although a deep, aching pain was still present, the burning sensation was totally gone.

(b) Administration to a Patient with Porphyria

Patient presented with lower extremity neuropathy from porphyria.

PLO gel was applied to legs. The pain level was 8/10. After ten minutes there was a small change to in pain, to 7.5/10. She was given several alternating inhalations of atrovent and albuterol and pain level dropped to 4/10. Patient noted that although deep pain was still present the stinging superficial pain had disappeared (c) Administration to a Patient with Neck Pain and Stiffness Patient presented with neck pain and stiffness with a pain level of 5/10 and lower back pain over the coccyx with a pain level of 8/10.

She was given Atrovent and noted that along with decreasing her neck pain to 3/10, her neck was much looser. There was no change in her back pain. PLO cream was applied to her back without change. Ultrasound was used with PLO cream on her back over the affected area but patient did not note a change in her pain level. Albuterol inhaler was given and, although there was no change in her back pain, her neck pain decreased to 2/10. Atrovent was then given and her neck pain decreased to 1/10. Patient also noted that her mobility in her neck was greatly improved (d) Administration to a Patient with Multiple Sclerosis and Sacroiliac Strain Patient presented with multiple sclerosis and sacroiliac strain with radiation into her legs. The pain level was 5410.

PLO cream was applied to back and pain decreased to 2/10. She was given an Atrovent inhaler and pain disappeared completely (e) Administration to a Patient Sacroiliac Strain Patient presented with sacroiliac strain with a pain level of 8.5/10.

Patient was given PLO cream and pain level decreased to 5110 and remained stable for over 5 minutes. Patient was given an Albuterol inhaler and pain level decreased to 4/10. Then he was given an Atrovent inhaler and pain level decreased to 3/10

(f) Administration to a Patient Sacroiliac Strain

Patient presented with midback pain with a pain level of 7/10.

PLO cream was administered to back with no change in pain level. Albuterol and Atrovent inhalers were given without any change (g) Administration to a Patient with Bilateral Plantar Fasciitis Patient with a diagnosis of bilateral plantar fasciitis with a pain level of 5/10 in both feet.

PLO cream was applied to right foot and pain level decreases to 0/10 in right foot, while pain in the left foot remained at 5/10. Patient was given Atrovent and pain in the left for decreased to 0/10.

(h) Administration to a Patient with Pain from Compression Fractures

Patient presented with pain from T11 and T12 compression fractures 6/10.

PLO cream was applied to her back and pain level dropped to O/10. No inhalers were used Patient presented with a possible lower lumbar compression fracture 5/10.

PLO cream was applied to back with no change in pain level. Albuterol inhaler was given and pain level dropped to 6/10.

The Examples below and Tables 2, 3, 4 and 5 show treatments which do not employ an active agent other than the lipophilic vehicle.

TABLE 2

Administration of LV's alone

| Patient (site of application) | Patient Complain | Pain Level Before | After |
|---|---|---|---|
| I. Treatment with HRT Base ||||
| [a]1 (left shoulder and back) | Rotator cuff tendinopathy | 9/10 | 0/10 |
| | Low Back pain | 4/10 | 3/10 |
| [b]2 (back) | Low back pain | 4/10 | 0/10 |
| [c]3 (left shoulder) | Supraspinatus Tendon tear | 4/10 | 2/10 |
| 4 (breast) | Nipple pain | 6/10 | 0/10 |
| 5 (inguinal region) | Lateral cutaneous femoral nerve syndrome | 4/10 | 0/10 |
| 7 | Shingles | 10/10 | 0/10 |
| 8 (thumb) | Gout | 7/10 | 0/10 |
| II. Treatment with Pluronic gel 20% with lecithin soya/isopropyl myristate ||||
| 1 (back) | Chest pain | 7/10 | 7/10 |
| 2 (shoulder and low back) | Rotator cuff tendinopathy | 10/10 | 0/10 |
| | Radicular back pain | 10/10 | 10/10 |
| 3 (neck) | Neck pain | 5/10 | 0/10 |
| 4 (ankle) | Ankle osteoarthritis | 7/10 | 0/10 |

TABLE 2-continued

Administration of LV's alone

| Patient (site of application) | Patient Complain | Pain Level Before | Pain Level After |
|---|---|---|---|
| 5 (ankle) | Ankle osteoarthritis | 7/10 | 0/10 |
| III. Treatment with VanPen | | | |
| *1 (left sacroiliac joint) | Bilateral sacroilitis | 10/10 | 5/10 |
| **2 (shoulder) | Reflex sympathetic dystrophy | 8/10 | 5.5/10 |
| 3 (scar on wrist) | Wrist pain from hypertrophic scar | 7/10 | 0/10 |
| IV Treatment with PLO gel | | | |
| 1 (scrotum and feet) | Bilateral tarsal tunnel syndrome | 7/10 | 0/10 |
| | Surgery to the scrotum | 10/10 | 0/10 |
| 2 (leg) | Reflex sympathetic dystrophy | 7/10 | 5/10 |
| V. Treatment with VersaCream | | | |
| 1 | Superficial thrombophlebitis | 10/10 | 0/10 |
| 2 | Pain in big toe from gout | 8/10 | 1/10 |

[a]Patient 1 noted that she felt more awake, lost her appetite and was breathing easier.
[b]Patient 2 experienced 30-40 increasing shoulder mobility. He also presented with nasal secretions which dried up with HRT base treatment.
[c]Patient 3 also presented with a greenish-black nipple discharge which disappeared with HRT treatment. She also noted that she felt much more alert, less congested, could breathe easier and was producing more saliva.
*Surgilube (placebo) treatment had no effect. Additional treatment with 20% pluronic gel decreased pain from 5/10 to 0/10.
**Patient noted increased salivation. Administration of Pluronic gel 20% decreased pain level from 5.5/10 to 4/10 and appetite went away. No additional effect was observed with this patient upon administration of treatment II.
(i) Patient noted marked loosening of neck and shoulders and increased ability to move them.

HRT was applied to a patient with rash and it took away the all itching for over 12 hours. No effect was observed upon administration of HRT to one patient with neck stiffness and itching.

The materials described in the table above generally contain compounds which are amphiphilic (i.e., contain polar and non-polar moieties within the molecule). For example, fatty acids, fatty acid esters, and lecithin are compounds which contains hydrophobic moiety (e.g. non-polar tail) and a hydrophilic moiety (e.g., carboxylic acid group, ester group, phosphate group). Lanolin is a complex mixture of esters of sterols, triterpene alcohols, and aliphatic alcohols. Oils which appear to have activity are rich in Omega 6 and/or Omega fatty acids.

Other molecules to evaluate include other fatty acids, cholesterol derivatives, and any materials rich in Omega 6 and Omega 9 fatty acids.

Example 35

Additional Treatments with Pluronic Gel 20% with Lecithin Soya/Isopropyl Myristate (a) Administration to a Patient with Cardiac Asthma and Hunger Pains Male hypertensive patient presented with labored breathing. Patient stated "I'm very hungry because I haven't eaten all day."

Pluronic gel 20% with lecithin soya/isopropyl myristate was applied to stomach and abdominal wall. Patient experienced 2 hours without any hunger pains or cravings. He also was breathing noticeably better. His peak flow meter measured 500 L/min before application of the cream and 600 L/min after its application. He also stated he felt much more awake and alert and his breathing remained better for the whole rest of the day (about 12 hours).

(b) Administration to a Patient with Shortness of Breath

Materials and Methods

Female patient with shortness of breath and hunger pains. Before Pluronic gel 20% with lecithin soya/isopropyl myristate was applied to abdomen, patient's peak expiratory flow was 240 L/min. After application of cream to abdomen and thorax, the patient's peak expiratory flow increased to 370 L/min. She also noted that she was able to breathe more deeply and easier. She also felt more awake as well as hot and sweaty and completely lost her appetite.

(c) Administration to a Patient with Hunger Pains

Female patient presented with hunger pains.

Treatment and Observation

Pluronic gel 20% with lecithin soya/isopropyl myristate was applied to stomach and abdominal wall. Patient noted that she was more awake and no longer hungry.

(d) Administration to a Patient with Shortness of Breath

Female asthmatic patient presented with audible wheezing and shortness of breath.

Before Pluronic gel 20% with lecithin soya/isopropyl myristate was applied to thorax, patient's peak expiratory flow was 180 L/min. After application of cream to thorax, the patient's peak expiratory flow increased to 240 U/min. She noted that she was able to breathe more easily and she was no longer wheezing. She also felt more awake as well as hot and sweaty and completely lost her appetite.

(e) Administration to a Patient with Hunger Pains

Female patient presented with hunger pains

After administration of Pluronic gel 20% with lecithin soya/isopropyl myristate to abdominal wall, patient noted that she completely lost her appetite.

(f) Administration Following a Fingerstick (i) Patient was given a fingerstick on right index finger without pluronic gel, which was painful; (blood sugar: 123 mg/dl), fingerstick on left index finger with pluronic gel 15% stick was less painful (blood sugar measured 132 mg/dl).

(ii) 15% pluronic was applied on the right index finger of a patient, and nothing was placed on the left index finger. A fingerstick was done on both fingers. The patient barely felt the needlestick on the right index finger, while on the left index finger he felt a sharp pain and discomfort which lingered even after the fingerstick. Applying 15% pluronic gel over this finger completely eliminated the discomfort. His glycemia measured on the left was 128 and on the right it was 114. When the blood was remeasured on other fingers without the gel, it was 109 on the left and 102 on the right.

iii) Finger sticks were performed on 20 patients using the TheraSense device glucometer. Although this device requires the smallest drop of blood and produces the least discomfort, it still results in a noticeable pain which lasts about ten to twenty minutes. To perform the finger stick, finger was cleaned with and alcohol wipe, allowed to dry, then a stick was performed and the glucose concentration measured. Using the same finger Pluronic gel 15%, allowed to dry, and a stick was performed. The pain was so reduced as to be barely noticeable and the meter reading was within 10% of the initial stick. Of note if the is the fact that the specifications for these meters allows for 20% variation for the device.

Example 36

Additional Treatments with PLO Cream and HRT Base (a) A patient presented with psoriasis. PLO cream on psoriatic plaques on back of hands and shins given over 1 month reduced their size.

(b) A patient presented with atopic dermatitis complaining of extreme pruritus. HRT cream base applied to rashy areas took away all itching for about 4-5 hours. Treatments using oils are shown in table 3 below.

TABLE 3

Treatment with oils; Overall analgesic effect with oils was immediate but duration of analgesia was significantly less than with creams.

| Patient | Patient Complain | Pain Level Before | Pain Level After |
|---|---|---|---|
| | I. Treatment with Oil of Cloves | | |
| 1 | Neck, shoulder and lower back pin | | 0/10 |
| 2 | Subscapular Bursitis secondary to Rotator cuff tendinopathy | 3/10 | 0/10 |
| 3 | Hip Bursitis | 8/10 | 0/10 |
| 4 | Neck pain and stiffness | 7/10 | 0/10 |
| *5 | Bilateral flank pain | 9/10 | 9/10 |
| | II. Treatment with Peppermint oil | | |
| [a]1 | SI Strain | 8/10 | 2/10 |
| [b]2 | Coccygodynia | 5/10 | 0/10 |
| | Neck stiffness and pain | 4/10 | 0/10 |
| [c]3 | Menstrual Cramps | 10/10 | 0/10 |
| [d]4 | Pain from Meniscal tear | 8/10 | 4/10 |
| [e]5 | Pain from Meniscal tear | 8/10 | 0/10 |
| [f]6 | Neck Pain | 8/10 | 2/10 |
| | Headache | 8/10 | 2/10 |
| 7 | Atherosclerotic peripheral vascular disease | 9/10 | 0/10 |
| [g]8 | Neck pain and Stiffness | 5/10 | 5/10 |
| [h]9 | Carpal tunnel Syndrome | 7/10 | 0/10 |

All oils used were pharmaceutical grade oils
*Additional PLO gel administration did not reduce pain level
[a]Patient noted decongestion, increased alertness, sweating and a sense of well being
[b]Patient noted numbness, decongestion, increased alertness, and loss of appetite
[c]Patient felt more awake, alert, and decongested (could breathe easier and more deeply)
[d]Patient felt more alert, awake and decongested
[e]Patient felt more mobile
[f]Patient felt more awake, decongested and was sweating
[g]Application of PLO eliminated the pain
[h]Patient started visibly sweating and her appetite disappeared Example 37

Treatment Using Combinations of Oil and LV's (a) Administration of VanPen with PLO to a Patient with Pain from neuroma and trochanteric bursitis.

A female patient presented with pain from a neuroma in her amputated stump in visible acute distress, and trochanteric bursitis. The pain level from the neuroma was 10+++/10 and from the trochanteric bursitis, 4/10.

VanPen mixed with PLO was applied to the stump. The pain level decreased to 51/10. When Sesame oil was applied to the stump, the pain decreased to 0. The patient stated that "The oil worked the best." Similarly, when Sesame oil was applied to the hip the pain disappeared.

(b) Application to a Patient with Pain from Inguinal Lymphadenopathy

A patient presented with an 8/10 pain level in the groin from right inguinal lymphadenopathy.

Application of PLO gel to groin eliminated all pain. Patient's blood sugar was also taken from two separate finger sticks. On one finger right pluronic gel 15% was applied on the other finger left nothing was applied. On the finger with pluronic gel the patient didn't feel the pain of the finger stick, on the other finger the patient felt the pain of the needlestick intensely. After application of pluronic gel to this finger the pain and sensitivity of the needlestick went away. The patient's blood sugar measured 116 mg/dl on the right and 111 mg/di on the left. Additional treatment combinations are shown in table 4.

Example 38

Administration of Oils Alone or in Combination with Other LV's

Table 5 shows the observations when oils were applied either alone or in combination with other LV's to human patients.

TABLE 4

Administration of Pluronic acid 20% (PA), lecithin/isopropyl myristate (L/I), Glycerin pure (GP) polyethylene glycol (PEG) and anhydrous Lanolin (LAN) alone or in combination

| Patient | Complaint (pain level) | PA | L/I | GP | PEG | LA | Observation |
|---|---|---|---|---|---|---|---|
| 1 | Neck pain and Stiffness (4/10) | + | + | + | + | | [x]Pain reduced to 2/10 |
| | | | + | + | + | + | [y]Pain reduced to 1/10 |
| 2 | Neck pain and Stiffness | + | | + | | | *No effect |
| 3 | Tarsal tunnel syndrome (8/10) | + | + | + | | | Pain reduced to 0/10 |
| **4 | Bilateral SI strain (8.5/10) | + | + | + | | | Pain reduced 0/10 |
| 5 | Pain in big toe (8/10) | | | + | | | No effect |
| | | | | | + | | + Pain reduced 4/10 |
| [a]6 | Knee Osteoarthritis (4/10) | | | + | | | + Pain reduced 0/10 |
| | Rotator Cuff Impingement (10/10) | | | + | | | + Pain reduced 1/10 |
| 7 | Neck pain | | | + | | | Pain disappeared |
| [b]8 | Rotator cuff tendinopathy | | | + | | | + Small to no effect |
| | Coccydynia | | | + | | | + Small to no effect |
| [c]9 | Carpal tunnel syndrome (4/10) | | | | | | + Pain reduced 2/10 |
| | Hip bursitis (4/10) | | | | | | + Pain reduced 2/10 |
| | Neck pain and stiffness (6/10) | | | | | | + Pain reduced 2/10 |
| [d]10 | Bilateral costochondritis (8/10) | | | + | | | + Pain reduced 6/10 |
| [e]11 | Systemic Lupus Erythematosis (6/10) | + | + | | + | | Pain reduced to 4/10 |

[x]Treatment included ultrasound application; Patient could not rotate head to the right past 70 degrees without pain
[y]Treatment included sesame oil; rotation to the right improved to about 88 degrees
*Treatment also included application of motor oil and grapeseed oil
**Patient had initially been hoarse. Treatment eliminated hoarseness, he felt less congested and more awake
[a]Patients pain level from osteoarthritis had been reduced from 6/10 to 4/10 by the administration of GP and then LAN
[b]With subsequent administration of PLO, shoulder pain disappeared
[c]prior administration of GP had no effect
[d]Pain level further decreased to 4/10 with VanPen administration. No further change was observed with a combination of VanPen and PLO or PLO alone.
[e]There was no effect on pain when cottonseed oil was added to the combination treatment

TABLE 5

Application of oils in combination with other LVs

| Patient | Complaint (pain level) | Treatment | Observation |
|---|---|---|---|
| 1 | Costalgia (7/10) and L3 radiculopathy to knee (5/10) | Olive, Peanut or Canola oil | No effect |
| | | Burts Bees | An effect, too small to quantify |
| | | Bag Balm | An effect, too small to quantify |
| | | Lecithin + PEG + PLO | Both pains decreased by 50%. Increased briskness of patellar reflex |
| 2 | Trigeminal neuralgia (TN) (2/10) and frontal headache (1/10) | Tween 80 | *Decreased TN pain to 1/10 and headache to 0/10 |
| 3 | Coccygodynia (5/10) | SDS 20% | **Reduced pain to 0/10 |
| 4 | Low back pain (4/10) | Peanut or Olive oil | No effect |
| | Rotator Cuff Syndrome (4/10) | Cotton seed oil | 50% reduction in pain; wore off in 10 min |
| 5 | Pain from neck spasm (5/10) | Cotton seed oil | Pain decreased to 3/10; effect wore off in 10 minutes |
| $^a$6 | Plantar fascitis and neck stiffness (2-3/10) | Cotton seed oil | Reduced pain in neck to 1/10; no effect on plantar fascitis |
| 7 | Lumbar radiculopathy (4/10) | Cotton seed oil | ***No effect |
| 8 | Rotator cuff syndrome (6/10) | Propylene glycol | No effect |
| | Knee Osteoarthritis (6/10) | Glycerin | Shoulder pain decreased from 6-4/10 No effect on knee |
| 9 | Neck stiffness (4/10) | Tween 80 | No effect |
| 10 | Neck pain (5/10) | Tween 80 | More mobility; no decrease in pain |
| | | SDS 20% | No change in pain or mobility |
| | | Triton x100 | Slight increase in mobility; no change in pain |
| | | Tween 20 | Increased mobility; no change in pain |
| | | Glycerin pure | Pain decreased to 1/10; Increased mobility for 1 hour |
| | | Propylene glycol | No effect |

*Effect lasted for 5 minutes upon first administration, but lasted until patient left upon second administration
**patient was jittery for several minutes, lost appetite and breathed better
***VanPen application resulted in a heating feeling with a 20-30% reduction in pain which lasted 5-6 hours
$^a$Patellar reflex were more brisk while ankle reflexes were less brisk Example 39

Administration of SDS, Tween and Dawn Dishwashing Liquid (a) A patient presented with congestion, wheezing and hunger. Application of SDS and Tween 80 led to an improvement in breathing. Administration of Dawn Hand Dishwashing Liquid led to a strong improvement in breathing. Patient completely lost appetite for over 8 hours.

(b) A Patient presented with a 5-6 tension headache and knuckle stiffness with 65 degree range of motion from side to side. With application of Dawn Hand Dishwashing Liquid, the patient was breathing easier, felt more awake, pain in neck and head were gone, and experienced greatly improved mobility with head turning almost reaching 90 degrees on each side (c) A patient presented with an 8/10 SI joint pain. Patient was taking Atenolol. Treatment with Dawn Hand Dishwashing Liquid had no effect.

(d) A patient presented with a 7/10 low back pain, abdominal cramps from menses, flank pain from Urinary Tract infection.

With application of Dawn Hand Dishwashing Liquid, patient was breathing better, awakened, less congested, pain decreased from 7/10 to 3/0. Dawn was applied to abdomen, right flank and low back.

Example 40

Administration of MonaVie Juice in Aquaphor Cream 50:50 Mixture Made by Weise Compounding Pharmacy A mixture of MonaVie juice in aquaphor cream was administered to patients with different conditions. The results are shown in table 6.

TABLE 6

Administration of MonaVie Juice in aquafor cream

| | | Pain level | |
|---|---|---|---|
| Patient | Complaint | Before | After |
| 1 | Coccygodynia | 8/10 | 6/10 |
| $^a$2 | Right rotator cuff tendinopathy | 7/10 | 0/10 |
| | Radicular low back pain | 5/10 | 4/10 |

TABLE 6-continued

Administration of MonaVie Juice in aquafor cream

| Patient | Complaint | Pain level Before | Pain level After |
|---|---|---|---|
| 3 | Low back pain and stiffness | 5/10 | 0/10 |
|  | Right ankle bruise from trauma | 4/10 | 1/10 |
| 4 | SI Strain | 7/10 | 5/10 |
|  | Neuroma in amputated thumb | 5/10 | 0/10 |
| 5 | Rotator cuff tendinopathy | 7/10 | 0/10 |
|  | L5 radiculopathy | 9/10 | 9/10 |

[a] Patient also presented with congestion and wheezing which was decreased with cream application. Subsequent application of PLO cream reduced pain on shoulder with no effect on lower back.

A summary of the treatments for pain, categorized by conditions treated is shown in table 7 below.

TABLE 7

SUMMARY TO TREATMENTS

| PT | TREATMENT | EFFECT ON PAIN LEVEL/% change | % Change in Pain level |
|---|---|---|---|
| (a) Rotator Cuff Tendinopathy (b) rotator cuff tear (c) shoulder pain | | | |
| 1(a) | PLO | Very slight effect | |
|  | PLO gel | From 4/10 to 3/10 | 25% |
| 2(a) | Clonidine 0.6 mg + NB | From 5/10 to 4/10 | 20% |
|  | VanPen | From 4/10 to 3/10 | 25% |
| 3(a) | Clonidine 0.8 mg | From 5/10 to 0/10 | 100% |
| 4(a) | Atenolol in PLO to back and shoulder | From 8/10 to 0/10 | 100% |
| 5(a) | Clonidine 0.6 mg + NB, then VanPen, Pluronic gel 20% with L/IM | No effect | 0 |
| 6(b) | Clonidine | No effect | 0 |
|  | Clonidine combined with nitrobid | From 8.5/10 to 7/10 | 18.75% |
| 7(b) | Nitropaste | From 6/10 to 3/10 | 50% |
|  | Clonidine paste | From 3/10 to 0/10 | 100% |
| 8(c) | HRT | From 9/10 to 0/10 | 100% |
| 9(b) | HRT | From 4/10 to 2/10 | 50% |
| 10(a) | Pluronic gel 20% with LS/IM | From 10/10 to 0/10 | 100% |
| 11(a) | PEG | From 9/10 to 0/10; | 100% |
| 12 | Oil of cloves | From 3/10 to 0/10 (from subscapular bursitis); | 100% |
| 13 | Glycerin pure + LAN | From 10/10 to 1/10 (rotator cuff impingement) | 90% |
| 14(a) | MJ/AQ cream in 50:50 | From 7/10 to 0/10 | 100% |
| 15 | Cottonseed oil | From 4/10 to 2/10; rotator cuff impingement) no effect with olive/peanut oil | 50% |

Summary: 9 patients experienced a 1-5 change in pain level, 6 patients a 7-10 change. 2 had no change

| Fibromyalgia | | | |
|---|---|---|---|
| 1 | Different combinations of creams | From 7/10 to 5.75/10 | 17.85% |

Summary: Change in pain was 2.25

| (a) Lupus (b) Gout (c) rheumatoid arthritis | | | |
|---|---|---|---|
| 1(a) | 0.8 mg clonidine 2% NB paste | From 6/10 to 5/10 | 16.7% |
| 2(b) | HRT base | From 7/10 to 0/10 | 100% |
| 3(c) | Pluronic gel + LS/IM | From 10/10 to 0/10 | 100% |
| 4(b) | Versa cream | From 8/10 to 1/10 | 87.5% |

Summary: 1 patient experienced a change in pain level of 1, and 3, a change of 7-10

| Tronchanteric Bursitis | | | |
|---|---|---|---|
| 1 | Atenolol | From 8/10 to 6/10 | 25% |
|  | Clonidine 0.8 mg + NB | No change; hip looser | 0 |
| 2 | Clonidine | From 8 to 5-6/10 | 31.25% |
| 3 | NB to trochanter | From 7/10 to 0/10 | 100% |
| 4 | Clonidine 8 mg | From 7/10 to 0/10 | 100% |

Summary: 1 patient experienced a 2-3 change in pain level, 2 patients a 7 change. 1 had no change.

TABLE 7-continued

Sacroiliac Strain (b) Bilateral sacroilitis

| | | | |
|---|---|---|---|
| 1 | Atenolol | No change | 0 |
| | VanPen | From 10/10 to 0/10 | 100% |
| 2 | Clonidine 0.6 mg + nitrobid | From 6/10 to 3/10 | 50% |
| 3 | Nitrobid | From 8/10 to 7/10 | 12.5% |
| 4 | Nitrobid | From 9/10 to 6/10 | 33% |
| | Clonidine paste | From 6/10 to 5/10 | 16.7%; *44% |
| 5 | Nitrobid | From 6/10 to 5/10 | 16.7% |
| | Clonidine paste | From 5/10 to 4.75/10 | 5%; *37.5% |
| 6 | Clonidine 0.6 mg + Nitrobid | From 6/10 to 2/10 | 66.7% |
| 7 | PLO cream | From 8.5/10 to 5/10 | 41% |
| | Albuterol inhaler | From 5/10 to 4/10 | 20% |
| | Atrovent inhaler | From 4/10 to 3/10 | 23%; *64.7% |
| 8 | PLO cream then albuterol, then atrovent | No change in 7/10 pain | 0 |
| 9 | PLO cream | From 5/10 to 2/10 | 60% |
| 10 | PLO cream, then albuterol, then atrovent | From 8.5/10 to 4/10, to 3/10 | 53% to *64.7% |
| 11(b) | VanPen, then Pluronic 20% | From 10/10 to 5/10 to 0/10 (left joint) | 50% to *100% |
| | Pluronic 60% | From 10/10 to 9/10 (right joint) | 10% |
| 12 | Pluronic acid 20%/LS/IM | From 8.5/10 to 0/10 | 100% |
| 13 | Peppermint oil | From 8/10 to 2/10 | 75% |
| 14 | MJ/AQ cream 50:50 | From 7/10 to 5/10 | 28.6% |

Summary: 10 patients experienced a 1-5 change in pain level, 8 experienced a 6-10 change, and 1, no change

Thoracalgia

| | | | |
|---|---|---|---|
| 1 | VanPen to left side | From 5/10 to 3/10 | 40% |
| | Atenolol to right side | Pain decreased to 2/10 | 60% |
| | Atenolol to left side and VanPen to right side | Pain disappeared completely | 100% |
| 2 | Pluronic gel 20% with LS/IM + NB | From 6/10 to 0/10 | 100% |
| 3 | Pluronic gel 20% with LS/IM | No change in 7/10 pain | 0 |

Summary: 2 patients experienced a 5-6 change in pain level; 1 patient had no change.

Osteoarthritis

| | | | |
|---|---|---|---|
| 1 | Atenolol to knee | From 8/10 to 5/10 | 37.5% |
| 2 | Nitrobid paste to knee | From 10/10 to 0/10 | 100% |
| 3 | Nitrobid paste to knee | From 10/10 to 0/10 | 100% |
| 4 | Clonidine paste | From 10/10 to 7/10 | 30% |
| | Nitrobid paste to knee | From 7/10 to 3.5/10 | 50%; *65% |
| 5 | Clonidine 8 mg | No change | 0 |
| | Nitrobid 2% to thumb | From 2/10 to 0/10 | 100% |
| 6 | Clonidine to right knee | From 6/10 to 3/10 | 50% |
| | Nitro to right knee | From 3/10 to 0/10 | *100% |
| | Nitro to left knee | No change | 0 |
| | Clonidine to left knee | 6/10 to 0/10 | 100% |
| 7 | Mix of Capsaicin + 2% viscous lidocaine | From 10/10 to 7/10 (left knee) | 30% |
| | | From 7/10 to 3/10 (right knee) | 57% |
| | Nitrobid paste | From 7/10 to 5/10 (left knee) | 28.5% * 50% |
| | | From 3/10 to 0/10 (right Knee) | *100% |
| 8 | Nitrobid paste | From 9/10 to 4/10 ((left knee) | 55.5% |
| | Clonidine paste | Pain went to zero | *100%; |
| 9 | Pluronic gel 20% with LS/IM | From 7/10 to 0/10 (ankle) | 100% |
| 10 | Pluronic gel 20% with LS/IM | From 7/10 to 0/10 (ankle) | 100% |
| 11 | PEG | From 9/10 to 0/10 (knee) | 100% |
| 12 | Glycerin pure | From 6/10 to 5/10 (right knee) | 16.7% |
| | Anhydrous lanolin | From 6/10 to 4/10 (left knee) | 33% |
| | Glycerin pure + anhydrous lanolin | Pain disappeared in both knees | *100% |
| 13 | Clonidine paste | From 5/10 to 3/10 (spondylosis) | 40% |
| | Nitrobid paste 2% | Pain went to zero | *100% |

Summary: 5 patients experienced a 2-6 change in pain, 8 patients experienced a 7-10 change TABLE 7-continued

| | | Bilateral plantar fascitis | |
|---|---|---|---|
| 1 | PLO cream | From 5/10 to 0/10 (right foot); no change on left | 100%; 0 |
| | Atrovent | Pain dropped from 5/10 to 0/10 (left | 100% |

Summary: Total change in pain was 5

| | | Compression Fracture of Vertebra | |
|---|---|---|---|
| 1 | 1.6 mg Clonidine | From 6/10 to 4/10, No change with NB | 33% |
| 2 | PLO cream | Pain dropped to zero (no initial value) | 100% |

Summary: One patient experienced a total change in pain of 2

| | | Neck Pain and stiffness | |
|---|---|---|---|
| 1 | Clonidine 0.8 mg | From 6/10 to 0/10 | 100% |
| 2 | PEG, then Oragel (to gums) | From 5/10 to 2/10, then to 1/10 | *80% |
| 3 | Atrovent inhaler, then albuterol inhaler, then atrovent | From 5/10 to 3/10, to 2/10, to 1/10 | *80% |
| 4 | Pluronic gel 20% with LS/IM | From 5/10 to 0/10 | 100% |
| 5 | PEG to gums | From 5/10 to 2/10 | 60% |
| 6 | Oil of cloves | From 7/10 to 0/10 | 100% |
| 7 | Glycerin pure + Pluronic acid 20% + motor oil + grapeseed oil | No change in pain level | 0 |
| 8 | Peppermint oil | From 4/10 to 0/10 | 100% |
| 9 | Peppermint oil; then PLO | No change, then From 5/10 to 0/10 (PLO) | 0; then 100% |
| 10 | Peppermint oil | From 8/10 to 0/10 | 100% |
| 11 | Glycerin pure, then Lanolin (LAN) | No effect (glycerin), From 6/10 to 3/10 (LAN) | |
| 12* | Cottonseed oil | From 5/10 to 3/10 (* neck spasm) | 40% |
| 13 | Nitrobid cream | From 9/10 to 6/10 (Torticollis) | 33% |
| 14 | Nitrobid paste to neck | From 9/10 to 0/10 (cervical strain) | 100% |

Summary: 10 patients experienced a 2-5 change in pain, 3 experienced a 7-9, change, 1 experienced no change

| | | Patellofemoral Syndrome | |
|---|---|---|---|
| 1 | Nitrobid | From 7/10 to 5/10 | 28.6% |
| | Clonidine 0.8 mg | From 5/10 to 3/10 | 40%; *57% |
| 2 | PEG to gums | No change in 7/10 pain | 0 |

Summary: One patient experienced a total change in pain of 4, one patient experienced no change

| | | (a) Migraine, (b) tension Headache, (c) cluster headache, (d) headache | |
|---|---|---|---|
| 1(a)(b) | NB paste, then clonidine paste | From 6/10 to 5/10, to 0/10 | *100% |
| 2(c) | Clonidine (1.6 mg) + 2% NG | From 10/10 to 0/10 | 100% |
| 3(d) | Clonidine (0.1 mg) + 2% NG | From 10/10 to 3/10 | 70% |
| 4(d) | Peppermint oil | From 8/10 to 2/10 | 75% |

Summary: Two patients experienced a change in pain of 6, two, a change in pain of 7-8

| | | (a) Tarsal Tunnel Syndrome (b) Carpal Tunnel Syndrome (c) wrist pain | |
|---|---|---|---|
| 1(a) | Lecithin Soya in IM | From 5/10 to 3/10 | 40% |
| 2(c) | VanPen | From 7/10 to 0/10 | 100% |
| 3(b) | Nitrobid paste to wrist | From 9/10 to 4/10 | 55.6% |
| 4(c) | PEG to gums | No change in 7/10 pain | 0 |
| 5(c) | PEG to wrist | From 8/10 to 0/10 (DeQuervains tenosynovitis) | 100% |
| 6(a) | PLO gel | From 7/10 to 0/10 | 100% |
| 7(a) | Glycerin pure + Pluronic acid 20%/LS/IM | From 8/10 to 0/10 | 100% |
| 8(b) | Peppermint oil | From 7/10 to 0/10 | 100% |
| 9(b) | Glycerin pure, then lanolin | No effect (glycerin); From 4/10 to 2/10 (LAN) | 0, then 50% |

Summary: 3 patients experienced a change in pain level of 2-5, 5, a change of 7-8 and 1, no change TABLE 7-continued Torn ACL and Meniscus

| | | | |
|---|---|---|---|
| 1 | Capsaicin and Lidocaine | From 8/10 to 7.5/10 | 6% |
| | Nitrobid paste | From 7.5/10 to 5/10 (knee) and 0/10 (ankle) | 33%; *37.5% (knee); *100% (ankle) |

Summary: The total change in pain was 3 at the knee and 8 at the ankle (a) Back (b) Leg Pain or (c) Joint pain (d) hip pain (e) toe pain (f) knee pain

| | | | |
|---|---|---|---|
| 1(a)(b) | Pluronic gel 20%, LS/IM mixed with NB | No change in 10/10 pain | 0 |
| 2(c) | Pluronic gel 20%, LS/IM mixed with NB | From 10/10 to 0/10 | 100% |
| 3(c) | Pluronic gel 20%, LS/IM mixed with NB | From 10/10 to 0/10 | 100% |
| 4(a) | HRT | From 4/10 to 3/10 | 25% |
| 5(a) | HRT | From 4/10 to 0/10 | 100% |
| 6(a) | PEG | From 9/10 to 0/10 (low back) | 100% |
| 7(c) | PEG to gums | From 7/10 to 4.5/10 | 35.7% |
| 8(d) | Oil of cloves | From 8/10 to 0/10 | 100% |
| 9(e) | Glycerin pure, the Lanolin (LAN) | No Change, then from 8/10 to 4/10 (LAN) | 0, then 50% |
| 10(f) | Peppermint oil | From 8/10 to 4/10 (meniscal tear) | 50% |
| 11(f0 | Peppermint oil | From 8/10 to 0/10 (meniscal tear) | 100% |
| 12(a) | MJ/AQ cream 50:50 | From 5/10 to 0/10 | 100% |
| 13(a) | MJ/AQ cream 50:50 | From 5/10 to 4/10 (radicular pain) | 20% |
| 14(a) | MJ/AQ cream 50:50 | No effect on 9/10 radiculopathy pain | 0 |
| 15 | MJ/AQ cream 50:50 | From 4/10 to 1/10 (ankle bruise) | 75% |
| 16(a) | Cottonseed oil | From 4/10 to 2/10; no effect with Peanut/olive oil | 50%; 0 |

Summary: 9 patients experienced a 1-5 change in pain, 6, a 7-10 change, and 2, no change (a) Diabetic neuropathy (b) Porphyric neuropathy (c) neuroma

| | | | |
|---|---|---|---|
| 1(a) | Oragel to gums | From 7/10 to 2/10 | 71% |
| 2(a) | PLO gel (heels) | From 8/10 to 5/10 (right); no change on left | 37.5% |
| | Albuterol inhaler (5 min later) | From 5/10 to 4/10 (right); 8/10 to 6/10 (left) | 20%; 25% |
| | Atrovent inhaler (5 min later) | 4/10 to 3/10 (right); 6/10 to 5/10 (left) | 25%; 16.7% |
| | Albuterol inhaler (5 min later) | 3/10 to 2/10 (right); 5/10 to 3/10 (right) | 33%; 40% |
| 3(b) | PLO gel | From 8/10 to 7.5/10 | 6% |
| | Alternating atrovent and albuterol inhalers | From 7.5/10 to 4/10 | 46.7%; *50% |
| 4(c) | MJ/AQ cream 50:50 | From 5/10 to 0/10 (amputated thumb) | 100% |
| 5(c) | VanPen mixed with PLO | From 10+++/10 to 5/10 (amputated stump) | ++++50% |
| | Sesame oil | From 5/10 to 0/10 | *100% |

Summary: 4 patients experienced a 1-5 change in pain level, and 1, a 10 change (a) Nipple pain (b) Scrotal pain (c) Menstrual Cramps (d) groin pain

| | | | |
|---|---|---|---|
| 1(a) | HRT | From 6/10 to 0/10 | 100% |
| 2(b) | PLO gel | From 7/10 to 0/10 | 100% |
| 3(c) | Peppermint oil | From 10/10 to 0/10 | 100% |
| 4(d) | PLO gel | From 8/10 to 0/10 | 100% |

Reflex Sympathetic dystrophy

Summary: one patient experienced a 6 change in pain level, 3, a 7-10 change

| | | | |
|---|---|---|---|
| 1 | VanPen, then Pluronic 20% with LS/IM to abdomen | From 8/10 to 5.5/10, to 4/10 | 43.7%, to *50% |
| 2 | PLO cream | From 7/10 to 5/10 | 28.6% |

Summary: Both patients experienced a 2-4 change in pain level

Peripheral vascular disease

| | | | |
|---|---|---|---|
| 1 | Peppermint oil | 9/10 to 0/10 | 100% |

Summary: There was a pain level change of 9

TABLE 7-continued

| | | Coccygodynia | |
|---|---|---|---|
| 1 | MJ/AQ cream 50:50 | From 8/10 to 6/10 | 25% |
| Summary: Patient experienced a pain level change of 2 | | | |
| | | Superficial Thrombophlebitis | |
| 1 | Versa cream | From 10/10 to 0/10 | 100% |
| Summary: Patient experienced a pain level change of 10 | | | |
| | | Shingles | |
| 1 | PLO cream, then HRT | worse (PLO), then From 10/10 to 0/10 (HRT) | 0; then 100% |
| 2 | Combination of different creams | None of the creams used worked | 0 |
| Summary: Patient experienced a pain level change of 10 | | | |
| | | Bilateral Costochondritis | |
| 1 | Lanolin + glycerin pure, then sesame oil | From 8/10 to 6/10, to 4/10 | 25% to *50% |
| Summary: Patient experienced a pain level change of 4 | | | |

Modifications and variations will be obvious to those of skill in the art from the foregoing detailed description of the invention and are intended to come within the scope of the following claims.

We claim:

1. A method for the treatment of pain in a subject, wherein the pain is selected from the group consisting of joint pain, surface somatic pain, and pain associated with an inflammatory arthropathy, bursitis, a tendinopathy, psoriasis, or muscle stiffness, the method consisting of:
    (a) topically administering to the skin, at or adjacent to the site in need of treatment for pain, an effective amount of a formulation consisting of:
        i) an active ingredient, as the only pain relieving active ingredient in the formulation, selected from the group consisting of lecithin, isopropyl palmitate, isopropyl myristate, and combinations thereof; and
        ii) an aqueous mixture of excipients to form a cream, gel, lotion, paste, suspension or dispersion, for topical application to the skin of the subject; to thereby alleviate pain in the subject, said excipients being one or more of:
        (a) cetyl alcohol,
        (b) stearyl alcohol,
        (c) glycerin monostearate,
        (d) stearic acid,
        (e) polyoxyl 40 stearate,
        (f) urea,
        (g) imidurea,
        (h) alkanols,
        (i) preservatives,
        (j) buffers, and
        (k) collodial insoluble skin protectant;
        wherein the formulation does not contain a pain relieving ingredient other than said active ingredient; and
    (b) optionally administering to the subject one or more additional therapies selected from the group consisting of iontophoresis, transcutaneous electrical nerve stimulation (TENS), muscle stimulation, diathermy, radiation therapy, infrared, ultraviolet and cold laser.

2. The method of claim 1, wherein the pain is joint pain.

3. The method of claim 1, further consisting of administering to the subject one or more additional therapies selected from the group consisting of iontophoresis, transcutaneous electrical nerve stimulation (TENS), muscle stimulation, diathermy, radiation therapy, infrared, ultraviolet and cold laser.

4. The method of claim 1, wherein the active ingredient is a combination of lecithin, isopropyl palmitate, and isopropyl myristate.

5. The method of claim 1, wherein the active ingredient is lecithin.

6. The method of claim 1, wherein the formulation has soya lecithin, isopropyl palmitate, steric acid, glycerin monostearate, isopropyl myristate, and polyoxyl 40 stearate.

7. The method of claim 1, wherein the formulation is in the form of a gel.

8. The method of claim 6, wherein the formulation is in the form of a gel.

9. The method of claim 1, wherein said pain in the subject is pain associated with an inflammatory arthropathy.

10. The method of claim 4, wherein said pain in the subject is pain associated with an inflammatory arthropathy.

11. The method of claim 8, wherein said pain in the subject is pain associated with an inflammatory arthropathy.

12. The method of claim 1, wherein said pain in the subject is pain associated with rheumatoid arthritis.

13. The method of claim 4, wherein said pain in the subject is pain associated with rheumatoid arthritis.

14. The method of claim 8, wherein said pain in the subject is pain associated with rheumatoid arthritis.

15. A method for the treatment of pain in a subject, wherein the pain is selected from the group consisting of joint pain, surface somatic pain, and pain associated with an inflammatory arthropathy, bursitis, a tendinopathy, psoriasis, or muscle stiffness, the method consisting of administering to the skin at or adjacent to the site in need of treatment an effective amount of a formulation consisting of i) lecithin, ii) optionally one or two penetration enhancer fatty acid ester compounds, and iii) an aqueous mixture of excipients to form a cream, gel, lotion, paste, suspension or dispersion for topical application to the skin of the subject; to thereby alleviate pain in the subject, said excipients being one or more of:
    (a) cetyl alcohol,
    (b) stearyl alcohol,
    (c) glycerin monostearate,
    (d) stearic acid,
    (e) polyoxyl 40 stearate,
    (f) urea, (g) imidurea,
(h) alkanols,
(i) preservatives,
(j) buffers, and
(k) collodial insoluble skin protectant.

16. The method of claim 15, wherein one or two penetration enhancer fatty acid ester compounds are present in the formulation.

17. The method of claim 16, wherein the formulation has one penetration enhancer fatty acid ester compound selected from the group consisting of isopropyl palmitate and isopropyl laurate.

18. The method of claim 17, wherein the penetration enhancer fatty acid ester compound is isopropyl palmitate.

19. The method of claim 15, wherein the formulation is in the form of a gel.

20. The method of claim 15, wherein said pain in the subject is pain associated with an inflammatory arthropathy.

21. The method of claim 18, wherein said pain in the subject is pain associated with an inflammatory arthropathy.

22. The method of claim 15, wherein said pain in the subject is pain associated with rheumatoid arthritis.

23. The method of claim 1, wherein the formulation has a preservative selected from the group consisting of methyl paraben and propyl paraben.

24. The method of claim 15, wherein the formulation has a preservative selected from the group consisting of methyl paraben and propyl paraben.

* * * * *